(12) United States Patent
Dempsey et al.

(10) Patent No.: US 12,152,243 B2
(45) Date of Patent: Nov. 26, 2024

(54) THERAPEUTIC COMPOSITIONS FOR TREATING PAIN VIA MULTIPLE TARGETS

(71) Applicant: Q-STATE BIOSCIENCES, INC., Cambridge, MA (US)

(72) Inventors: Graham T. Dempsey, Cambridge, MA (US); Owen McManus, Belmont, MA (US); Hongkang Zhang, Wellesley, MA (US); David Gerber, Cambridge, MA (US); Pin Liu, Cambridge, MA (US); Dawei Zhang, Cambridge, MA (US); Duncan Brown, Cambridge, MA (US); Sudhir Agrawal, Cambridge, MA (US); Caitlin Lewarch, Cambridge, MA (US)

(73) Assignee: QuellTx, Inc., Cambridge, MA (US)

( * ) Notice: Subject to any disclaimer, the term of this patent is extended or adjusted under 35 U.S.C. 154(b) by 0 days.

(21) Appl. No.: 17/478,219

(22) Filed: Sep. 17, 2021

(65) Prior Publication Data

US 2022/0112496 A1    Apr. 14, 2022

Related U.S. Application Data

(60) Provisional application No. 63/180,875, filed on Apr. 28, 2021, provisional application No. 63/079,912, filed on Sep. 17, 2020.

(51) Int. Cl.
*C07H 21/04* (2006.01)
*A61K 31/7088* (2006.01)
*C12N 15/113* (2010.01)

(52) U.S. Cl.
CPC ........ *C12N 15/113* (2013.01); *A61K 31/7088* (2013.01); *C12N 2310/11* (2013.01); *C12N 2310/315* (2013.01); *C12N 2310/321* (2013.01); *C12N 2310/3341* (2013.01); *C12N 2310/335* (2013.01); *C12N 2310/341* (2013.01); *C12N 2310/346* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 6,617,442 B1 | 9/2003 | Crooke et al. | |
| 7,250,496 B2 | 7/2007 | Bentwich | |
| 7,341,835 B2 | 3/2008 | Blume et al. | |
| 7,563,586 B2 | 7/2009 | Okuse et al. | |
| 7,582,745 B2 | 9/2009 | Sah et al. | |
| 7,618,814 B2 | 11/2009 | Bentwich | |
| 7,629,321 B2 | 12/2009 | Crooke | |
| 7,659,082 B2 | 2/2010 | MacDonald et al. | |
| 7,687,617 B2 | 3/2010 | Thrue et al. | |
| 7,695,902 B2 | 4/2010 | Crooke | |
| 7,709,616 B2 | 5/2010 | Bentwich et al. | |
| 7,786,291 B2 | 8/2010 | Goregaoker et al. | |
| 7,901,882 B2 | 3/2011 | Cao et al. | |
| 7,902,168 B2 | 3/2011 | Sah et al. | |
| 8,178,503 B2 | 5/2012 | Rigoutsos et al. | |
| 8,183,221 B2 | 5/2012 | Thakker et al. | |
| 8,309,703 B2 | 11/2012 | Goregaoker et al. | |
| 8,410,054 B2 | 4/2013 | MacDonald et al. | |
| 8,461,315 B2 | 6/2013 | Benwich et al. | |
| 8,481,701 B2 | 7/2013 | Jarrige-Le Prado et al. | |
| 8,709,716 B2 | 4/2014 | Cao et al. | |
| 8,729,045 B2 | 5/2014 | Goregaoker et al. | |
| 9,133,453 B2 | 9/2015 | Bentwich et al. | |
| 9,650,679 B2 | 5/2017 | Bentwich et al. | |
| 9,650,680 B2 | 5/2017 | Bentwich et al. | |
| 9,771,579 B2 | 9/2017 | Collard et al. | |
| 9,777,275 B2 | 10/2017 | Woolf et al. | |
| 9,828,640 B2 | 11/2017 | Cao et al. | |
| 9,944,699 B2 | 4/2018 | Crest et al. | |
| 10,072,076 B2 | 9/2018 | MacDonald et al. | |
| 10,415,038 B2 | 9/2019 | Guo et al. | |
| 11,459,587 B2 * | 10/2022 | Lundberg | A61K 35/30 |
| 2004/0097440 A1 | 5/2004 | Bennett | |
| 2005/0244851 A1 | 11/2005 | Blume et al. | |
| 2008/0125583 A1 | 5/2008 | Rigoutsos et al. | |
| 2013/0011922 A1 | 1/2013 | Quay et al. | |
| 2017/0240904 A1 | 8/2017 | Tallent et al. | |
| 2017/0319715 A1 | 11/2017 | Towne et al. | |
| 2017/0355990 A1 | 12/2017 | Collard et al. | |
| 2019/0010491 A1 | 1/2019 | Bentwich et al. | |
| 2019/0153477 A1 | 5/2019 | Lundberg et al. | |
| 2019/0224340 A1 | 7/2019 | Lundberg et al. | |

(Continued)

FOREIGN PATENT DOCUMENTS

| EP | 1569661 A2 | 9/2005 |
|---|---|---|
| EP | 1784501 A2 | 5/2007 |

(Continued)

OTHER PUBLICATIONS

Anderson, 2018, CRISPR off-target analysis in genetically engineered rats and mice, Natural Methods, 15(7):512-514.

(Continued)

*Primary Examiner* — Kimberly Chong
(74) *Attorney, Agent, or Firm* — Withers Bergman LLP; Thomas C. Meyers

(57) ABSTRACT

The invention provides non-opioid pain therapeutic compositions that include an antisense oligonucleotide (ASO) complementary to an identified target on a NaV channel mRNA. The ASO hybridizes to its target RNA and forms a duplex that recruits RNase H to degrade the RNA, thereby downregulating NaV channel synthesis, which inhibits the neuron's ability to contribute to the perception of pain. The ASO targets one of the specific identified targets, and may be provided as a gapmer that includes a central DNA segment flanked by modified RNA wings. When the composition is delivered to dorsal root ganglion (DRG) neurons in vitro, the DRG neurons exhibit a dose-dependent knockdown of NaV1.7, NaV1.8, or NaV1.9.

19 Claims, 9 Drawing Sheets

Specification includes a Sequence Listing.

(56) References Cited

U.S. PATENT DOCUMENTS

| | | |
|---|---|---|
| 2019/0270990 A1 | 9/2019 | Kordasiewicz et al. |
| 2019/0345573 A1 | 11/2019 | Khvorova et al. |
| 2022/0112496 A1 | 4/2022 | Dempsey et al. |

FOREIGN PATENT DOCUMENTS

| | | |
|---|---|---|
| EP | 2141233 A1 | 1/2010 |
| EP | 2284269 A2 | 2/2011 |
| EP | 2752488 A2 | 7/2014 |
| WO | 2002/068579 A2 | 9/2002 |
| WO | 2005/111211 A2 | 11/2005 |
| WO | 2006/047687 A2 | 5/2006 |
| WO | 2007/056326 A2 | 5/2007 |
| WO | 2009/143277 A2 | 11/2009 |
| WO | 2013/162363 A1 | 10/2013 |
| WO | 2016/011080 A2 | 1/2016 |
| WO | 2016/027168 A2 | 2/2016 |
| WO | 2017/209575 A1 | 12/2017 |
| WO | 2018/007976 A1 | 1/2018 |
| WO | 2018/007980 A1 | 1/2018 |
| WO | 2018/098328 A1 | 5/2018 |
| WO | 2018/165504 A1 | 9/2018 |
| WO | 2019/243430 A1 | 12/2019 |
| WO | 2020/191153 A2 | 9/2020 |
| WO | 2022/061108 A2 | 3/2022 |
| WO | 2022232395 | 11/2022 |

OTHER PUBLICATIONS

Int Search Report and Written Op mailed Oct. 14, 2022, for Int Application No. PCT/US2022/26738, filed Apr. 28, 2022 (28 pages).
Martinez-Moreno, 2017, Regulation of peripheral myelination through transcriptional buffering of Egr2 by an antisense long noncoding RNA, Cell Rep 20(8):1950-1963, 28 pages.
Int. Search Rpt. & Writt. Op. mailed Mar. 14, 2022, for PCT/US21/50866, filed Sep. 17, 2021 (12 pages).
Yu, 2011, Antisense-mediated knockdown of NaV1.8, but not NaV1.9, generates inhibitory effects on complete Freund's adjuvant-induced inflammatory pain in rat, PLOSOne 6(5):e19865.

* cited by examiner

- Nav1.x ASOs have high potency and subtype selectivity
- 450 nM cocktail ASO (150 nM Nav1.7 ASO + 150 nM Nav1.8 ASO + 150 nM Nav1.9 ASO) can knockdown all the three targets

SEQUENCE LISTING

```
<160> NUMBER OF SEQ ID NOS: 165

<210> SEQ ID NO 1
<211> LENGTH: 20
<212> TYPE: DNA
<213> ORGANISM: Artificial Sequence
<220> FEATURE:
<223> OTHER INFORMATION: ASO

<400> SEQUENCE: 1
gccagttcca cgggtcacga                                               20

<210> SEQ ID NO 2
<211> LENGTH: 20
<212> TYPE: DNA
<213> ORGANISM: Artificial Sequence
<220> FEATURE:
<223> OTHER INFORMATION: ASO

<400> SEQUENCE: 2
atccagccag ttccacgggt                                               20

<210> SEQ ID NO 3
<211> LENGTH: 20
<212> TYPE: DNA
<213> ORGANISM: Artificial Sequence
<220> FEATURE:
```

```
<223> OTHER INFORMATION: ASO

<400> SEQUENCE: 3
caggtgtacc cctctggaca                                               20

<210> SEQ ID NO 4
<211> LENGTH: 20
<212> TYPE: DNA
<213> ORGANISM: Artificial Sequence
<220> FEATURE:
<223> OTHER INFORMATION: ASO

<400> SEQUENCE: 4
agcacgcagc gtctgttggt                                               20

<210> SEQ ID NO 5
<211> LENGTH: 20
<212> TYPE: DNA
<213> ORGANISM: Artificial Sequence
<220> FEATURE:
<223> OTHER INFORMATION: ASO

<400> SEQUENCE: 5
tgccagcagc acgcagcgtc                                               20

<210> SEQ ID NO 6
<211> LENGTH: 20
<212> TYPE: DNA
<213> ORGANISM: Artificial Sequence
<220> FEATURE:
<223> OTHER INFORMATION: ASO

<400> SEQUENCE: 6
ttgccagcag cacgcagcgt                                               20

<210> SEQ ID NO 7
<211> LENGTH: 20
<212> TYPE: DNA
<213> ORGANISM: Artificial Sequence
<220> FEATURE:
<223> OTHER INFORMATION: ASO

<400> SEQUENCE: 7
tttgccagca gcacgcagcg                                               20

<210> SEQ ID NO 8
<211> LENGTH: 20
<212> TYPE: DNA
<213> ORGANISM: Artificial Sequence
<220> FEATURE:
<223> OTHER INFORMATION: ASO

<400> SEQUENCE: 8
gttttgccag cagcacgcag                                               20

<210> SEQ ID NO 9
<211> LENGTH: 20
<212> TYPE: DNA
<213> ORGANISM: Artificial Sequence
<220> FEATURE:
<223> OTHER INFORMATION: ASO

<400> SEQUENCE: 9
gtttgcctgg ttctgttctt                                               20
```

```
<210> SEQ ID NO 10
<211> LENGTH: 20
<212> TYPE: DNA
<213> ORGANISM: Artificial Sequence
<220> FEATURE:
<223> OTHER INFORMATION: ASO

<400> SEQUENCE: 10
tgtgctcgcc tatgcccttc                                               20

<210> SEQ ID NO 11
<211> LENGTH: 20
<212> TYPE: DNA
<213> ORGANISM: Artificial Sequence
<220> FEATURE:
<223> OTHER INFORMATION: ASO

<400> SEQUENCE: 11
gttctgctgc ttcgccttgc                                               20

<210> SEQ ID NO 12
<211> LENGTH: 20
<212> TYPE: DNA
<213> ORGANISM: Artificial Sequence
<220> FEATURE:
<223> OTHER INFORMATION: ASO

<400> SEQUENCE: 12 cccettctgc tctcattgtc                                               20

<210> SEQ ID NO 13
<211> LENGTH: 20
<212> TYPE: DNA
<213> ORGANISM: Artificial Sequence
<220> FEATURE:
<223> OTHER INFORMATION: ASO

<400> SEQUENCE: 13
gccccttctg ctctcattgt                                               20

<210> SEQ ID NO 14
<211> LENGTH: 20
<212> TYPE: DNA
<213> ORGANISM: Artificial Sequence
<220> FEATURE:
<223> OTHER INFORMATION: ASO

<400> SEQUENCE: 14
gagccccttc tgctctcatt                                               20

<210> SEQ ID NO 15
<211> LENGTH: 20
<212> TYPE: DNA
<213> ORGANISM: Artificial Sequence
<220> FEATURE:
<223> OTHER INFORMATION: ASO

<400> SEQUENCE: 15
gtgagcccct tctgctctca                                               20

<210> SEQ ID NO 16
<211> LENGTH: 20
<212> TYPE: DNA
<213> ORGANISM: Artificial Sequence
<220> FEATURE:
<223> OTHER INFORMATION: ASO
```

```
<400> SEQUENCE: 16
agtgagcccc ttctgctctc                                              20

<210> SEQ ID NO 17
<211> LENGTH: 20
<212> TYPE: DNA
<213> ORGANISM: Artificial Sequence
<220> FEATURE:
<223> OTHER INFORMATION: ASO

<400> SEQUENCE: 17
actgctgcgt cgctcctggg                                              20

<210> SEQ ID NO 18
<211> LENGTH: 20
<212> TYPE: DNA
<213> ORGANISM: Artificial Sequence
<220> FEATURE:
<223> OTHER INFORMATION: ASO

<400> SEQUENCE: 18
gcattttccc gttcaccggc                                              20

<210> SEQ ID NO 19
<211> LENGTH: 20
<212> TYPE: DNA
<213> ORGANISM: Artificial Sequence
<220> FEATURE:
<223> OTHER INFORMATION: ASO

<400> SEQUENCE: 19
tgcagtccac agcactgtgc                                              20

<210> SEQ ID NO 20
<211> LENGTH: 20
<212> TYPE: DNA
<213> ORGANISM: Artificial Sequence
<220> FEATURE:
<223> OTHER INFORMATION: ASO

<400> SEQUENCE: 20
gcatgagggc tgagcgtcca                                              20

<210> SEQ ID NO 21
<211> LENGTH: 20
<212> TYPE: DNA
<213> ORGANISM: Artificial Sequence
<220> FEATURE:
<223> OTHER INFORMATION: ASO

<400> SEQUENCE: 21
ctctcagggc tgcttctttt                                              20

<210> SEQ ID NO 22
<211> LENGTH: 20
<212> TYPE: DNA
<213> ORGANISM: Artificial Sequence
<220> FEATURE:
<223> OTHER INFORMATION: ASO

<400> SEQUENCE: 22
ctgtttgcca gcttccaagt                                              20

<210> SEQ ID NO 23
<211> LENGTH: 20
```

```
<212> TYPE: DNA
<213> ORGANISM: Artificial Sequence
<220> FEATURE:
<223> OTHER INFORMATION: ASO

<400> SEQUENCE: 23
ttggtccagt ccggtgggtt                                               20

<210> SEQ ID NO 24
<211> LENGTH: 20
<212> TYPE: DNA
<213> ORGANISM: Artificial Sequence
<220> FEATURE:
<223> OTHER INFORMATION: ASO

<400> SEQUENCE: 24
ttgcctcagc ttcttcttgc                                               20

<210> SEQ ID NO 25
<211> LENGTH: 20
<212> TYPE: DNA
<213> ORGANISM: Artificial Sequence
<220> FEATURE:
<223> OTHER INFORMATION: ASO

<400> SEQUENCE: 25
gttgcagtcc acagcactgt                                               20

<210> SEQ ID NO 26
<211> LENGTH: 20
<212> TYPE: DNA
<213> ORGANISM: Artificial Sequence
<220> FEATURE:
<223> OTHER INFORMATION: ASO

<400> SEQUENCE: 26
aggttaccta gagcccctac                                               20

<210> SEQ ID NO 27
<211> LENGTH: 20
<212> TYPE: DNA
<213> ORGANISM: Artificial Sequence
<220> FEATURE:
<223> OTHER INFORMATION: ASO

<400> SEQUENCE: 27
ggttgtttgc atcagggtct                                               20

<210> SEQ ID NO 28
<211> LENGTH: 20
<212> TYPE: DNA
<213> ORGANISM: Artificial Sequence
<220> FEATURE:
<223> OTHER INFORMATION: ASO

<400> SEQUENCE: 28
aggttcagcc tctgcttctt                                               20

<210> SEQ ID NO 29
<211> LENGTH: 20
<212> TYPE: DNA
<213> ORGANISM: Artificial Sequence
<220> FEATURE:
<223> OTHER INFORMATION: ASO

<400> SEQUENCE: 29
```
cttggacccc agcttttca                                         20

<210> SEQ ID NO 30
<211> LENGTH: 20
<212> TYPE: DNA
<213> ORGANISM: Artificial Sequence
<220> FEATURE:
<223> OTHER INFORMATION: ASO

<400> SEQUENCE: 30
gggttaccac agtctccttc                                        20

<210> SEQ ID NO 31
<211> LENGTH: 20
<212> TYPE: DNA
<213> ORGANISM: Artificial Sequence
<220> FEATURE:
<223> OTHER INFORMATION: ASO

<400> SEQUENCE: 31
gaatccatct ccccactctc                                        20

<210> SEQ ID NO 32
<211> LENGTH: 20
<212> TYPE: DNA
<213> ORGANISM: Artificial Sequence
<220> FEATURE:
<223> OTHER INFORMATION: ASO

<400> SEQUENCE: 32
gctgcccacc tttcttagga                                        20

<210> SEQ ID NO 33
<211> LENGTH: 20
<212> TYPE: DNA
<213> ORGANISM: Artificial Sequence
<220> FEATURE:
<223> OTHER INFORMATION: ASO

<400> SEQUENCE: 33
gccaattccc tggccatcct                                        20

<210> SEQ ID NO 34
<211> LENGTH: 20
<212> TYPE: DNA
<213> ORGANISM: Artificial Sequence
<220> FEATURE:
<223> OTHER INFORMATION: ASO

<400> SEQUENCE: 34
ccttgggatc tctgccaggt                                        20

<210> SEQ ID NO 35
<211> LENGTH: 20
<212> TYPE: DNA
<213> ORGANISM: Artificial Sequence
<220> FEATURE:
<223> OTHER INFORMATION: ASO

<400> SEQUENCE: 35
gtccctggag tcttgtctga                                        20

<210> SEQ ID NO 36
<211> LENGTH: 20
<212> TYPE: DNA
<213> ORGANISM: Artificial Sequence

<220> FEATURE:
<223> OTHER INFORMATION: ASO

<400> SEQUENCE: 36
ctcccatatc tccagtctgc                                                 20

<210> SEQ ID NO 37
<211> LENGTH: 20
<212> TYPE: DNA
<213> ORGANISM: Artificial Sequence
<220> FEATURE:
<223> OTHER INFORMATION: ASO

<400> SEQUENCE: 37
gctcttgctc tggttcagct                                                 20

<210> SEQ ID NO 38
<211> LENGTH: 20
<212> TYPE: DNA
<213> ORGANISM: Artificial Sequence
<220> FEATURE:
<223> OTHER INFORMATION: ASO

<400> SEQUENCE: 38
ggttcttcca gcttctctgc                                                 20

<210> SEQ ID NO 39
<211> LENGTH: 20
<212> TYPE: DNA
<213> ORGANISM: Artificial Sequence
<220> FEATURE:
<223> OTHER INFORMATION: ASO

<400> SEQUENCE: 39
catgtccctg tccatcccta                                                 20

<210> SEQ ID NO 40
<211> LENGTH: 20
<212> TYPE: DNA
<213> ORGANISM: Artificial Sequence
<220> FEATURE:
<223> OTHER INFORMATION: ASO

<400> SEQUENCE: 40
gtgtggcagc agtgaccagt                                                 20

<210> SEQ ID NO 41
<211> LENGTH: 20
<212> TYPE: DNA
<213> ORGANISM: Artificial Sequence
<220> FEATURE:
<223> OTHER INFORMATION: ASO

<400> SEQUENCE: 41
cccttgtgct gggtctatgt                                                 20

<210> SEQ ID NO 42
<211> LENGTH: 20
<212> TYPE: DNA
<213> ORGANISM: Artificial Sequence
<220> FEATURE:
<223> OTHER INFORMATION: ASO

<400> SEQUENCE: 42
gctctaccct agctgtcagg                                                 20

<210> SEQ ID NO 43
<211> LENGTH: 20
<212> TYPE: DNA
<213> ORGANISM: Artificial Sequence
<220> FEATURE:
<223> OTHER INFORMATION: ASO

<400> SEQUENCE: 43
gctcctcctc agagttttgc                                              20

<210> SEQ ID NO 44
<211> LENGTH: 20
<212> TYPE: DNA
<213> ORGANISM: Artificial Sequence
<220> FEATURE:
<223> OTHER INFORMATION: ASO

<400> SEQUENCE: 44
gagcctcttc tcttcaggcc                                              20

<210> SEQ ID NO 45
<211> LENGTH: 20
<212> TYPE: DNA
<213> ORGANISM: Artificial Sequence
<220> FEATURE:
<223> OTHER INFORMATION: ASO

<400> SEQUENCE: 45
tggctcatcc aggctcatca                                              20

<210> SEQ ID NO 46
<211> LENGTH: 20
<212> TYPE: DNA
<213> ORGANISM: Artificial Sequence
<220> FEATURE:
<223> OTHER INFORMATION: ASO

<400> SEQUENCE: 46
gcattattcc caccaggtcc                                              20

<210> SEQ ID NO 47
<211> LENGTH: 20
<212> TYPE: DNA
<213> ORGANISM: Artificial Sequence
<220> FEATURE:
<223> OTHER INFORMATION: ASO

<400> SEQUENCE: 47
tctcttcagt ctcctccaca                                              20

<210> SEQ ID NO 48
<211> LENGTH: 20
<212> TYPE: DNA
<213> ORGANISM: Artificial Sequence
<220> FEATURE:
<223> OTHER INFORMATION: ASO

<400> SEQUENCE: 48
ccagcagttg gcagaggttc                                              20

<210> SEQ ID NO 49
<211> LENGTH: 20
<212> TYPE: DNA
<213> ORGANISM: Artificial Sequence
<220> FEATURE:
<223> OTHER INFORMATION: ASO

<400> SEQUENCE: 49
gcttgtgcat cccagtgcct                                               20

<210> SEQ ID NO 50
<211> LENGTH: 20
<212> TYPE: DNA
<213> ORGANISM: Artificial Sequence
<220> FEATURE:
<223> OTHER INFORMATION: ASO

<400> SEQUENCE: 50
cctccatctg attcctcctc                                               20

<210> SEQ ID NO 51
<211> LENGTH: 20
<212> TYPE: DNA
<213> ORGANISM: Artificial Sequence
<220> FEATURE:
<223> OTHER INFORMATION: ASO

<400> SEQUENCE: 51
gccttctcac cagtgctgct                                               20

<210> SEQ ID NO 52
<211> LENGTH: 20
<212> TYPE: DNA
<213> ORGANISM: Artificial Sequence
<220> FEATURE:
<223> OTHER INFORMATION: ASO

<400> SEQUENCE: 52
tctagccttc tcaccagtgc                                               20

<210> SEQ ID NO 53
<211> LENGTH: 20
<212> TYPE: DNA
<213> ORGANISM: Artificial Sequence
<220> FEATURE:
<223> OTHER INFORMATION: ASO

<400> SEQUENCE: 53
ggtggcaggt caagcagggt                                               20

<210> SEQ ID NO 54
<211> LENGTH: 20
<212> TYPE: DNA
<213> ORGANISM: Artificial Sequence
<220> FEATURE:
<223> OTHER INFORMATION: ASO

<400> SEQUENCE: 54
tcttggtcct tctgctccct                                               20

<210> SEQ ID NO 55
<211> LENGTH: 20
<212> TYPE: DNA
<213> ORGANISM: Artificial Sequence
<220> FEATURE:
<223> OTHER INFORMATION: ASO

<400> SEQUENCE: 55
gctccccgat cagttctgct                                               20

<210> SEQ ID NO 56

```
<211> LENGTH: 20
<212> TYPE: DNA
<213> ORGANISM: Artificial Sequence
<220> FEATURE:
<223> OTHER INFORMATION: ASO

<400> SEQUENCE: 56
tgtccggtgt gtgctgtaga                                        20

<210> SEQ ID NO 57
<211> LENGTH: 20
<212> TYPE: DNA
<213> ORGANISM: Artificial Sequence
<220> FEATURE:
<223> OTHER INFORMATION: ASO

<400> SEQUENCE: 57
tggtcctccc tttgttcagc                                        20

<210> SEQ ID NO 58
<211> LENGTH: 20
<212> TYPE: DNA
<213> ORGANISM: Artificial Sequence
<220> FEATURE:
<223> OTHER INFORMATION: ASO

<400> SEQUENCE: 58
gttgcagccc caccaaggca                                        20

<210> SEQ ID NO 59
<211> LENGTH: 20
<212> TYPE: DNA
<213> ORGANISM: Artificial Sequence
<220> FEATURE:
<223> OTHER INFORMATION: ASO

<400> SEQUENCE: 59
gggtctgctg gtagaggcgt                                        20

<210> SEQ ID NO 60
<211> LENGTH: 20
<212> TYPE: DNA
<213> ORGANISM: Artificial Sequence
<220> FEATURE:
<223> OTHER INFORMATION: ASO

<400> SEQUENCE: 60
gcacctcctg ctccttccgg                                        20

<210> SEQ ID NO 61
<211> LENGTH: 20
<212> TYPE: DNA
<213> ORGANISM: Artificial Sequence
<220> FEATURE:
<223> OTHER INFORMATION: ASO

<400> SEQUENCE: 61
gttgtcttct gtggagccct                                        20

<210> SEQ ID NO 62
<211> LENGTH: 20
<212> TYPE: DNA
<213> ORGANISM: Artificial Sequence
<220> FEATURE:
<223> OTHER INFORMATION: ASO

<400> SEQUENCE: 62
```
gctggtcaag cagggtgggc                                                    20

<210> SEQ ID NO 63
<211> LENGTH: 20
<212> TYPE: DNA
<213> ORGANISM: Artificial Sequence
<220> FEATURE:
<223> OTHER INFORMATION: ASO

<400> SEQUENCE: 63
ggccacgccc agctctagca                                                    20

<210> SEQ ID NO 64
<211> LENGTH: 20
<212> TYPE: DNA
<213> ORGANISM: Artificial Sequence
<220> FEATURE:
<223> OTHER INFORMATION: ASO

<400> SEQUENCE: 64
ggtgaggttc cccagtgccc                                                    20

<210> SEQ ID NO 65
<211> LENGTH: 20
<212> TYPE: DNA
<213> ORGANISM: Artificial Sequence
<220> FEATURE:
<223> OTHER INFORMATION: ASO

<400> SEQUENCE: 65
gtcgtgcatg tgccagcggg                                                    20

<210> SEQ ID NO 66
<211> LENGTH: 20
<212> TYPE: DNA
<213> ORGANISM: Artificial Sequence
<220> FEATURE:
<223> OTHER INFORMATION: ASO

<400> SEQUENCE: 66
tccgtgccag ggccacctgc                                                    20

<210> SEQ ID NO 67
<211> LENGTH: 20
<212> TYPE: DNA
<213> ORGANISM: Artificial Sequence
<220> FEATURE:
<223> OTHER INFORMATION: ASO

<400> SEQUENCE: 67
gggagcttgg agccctccag                                                    20

<210> SEQ ID NO 68
<211> LENGTH: 20
<212> TYPE: DNA
<213> ORGANISM: Artificial Sequence
<220> FEATURE:
<223> OTHER INFORMATION: ASO

<400> SEQUENCE: 68
gttccagtgc ctgggctcct                                                    20

<210> SEQ ID NO 69
<211> LENGTH: 20
<212> TYPE: DNA

```
<213> ORGANISM: Artificial Sequence
<220> FEATURE:
<223> OTHER INFORMATION: ASO

<400> SEQUENCE: 69
ccagctcagg gatcttcctc                                                    20

<210> SEQ ID NO 70
<211> LENGTH: 20
<212> TYPE: DNA
<213> ORGANISM: Artificial Sequence
<220> FEATURE:
<223> OTHER INFORMATION: ASO

<400> SEQUENCE: 70
gtcttgcgca cctgccagcc                                                    20

<210> SEQ ID NO 71
<211> LENGTH: 20
<212> TYPE: DNA
<213> ORGANISM: Artificial Sequence
<220> FEATURE:
<223> OTHER INFORMATION: ASO

<400> SEQUENCE: 71
cgtgggcttc tggtccaggt                                                    20

<210> SEQ ID NO 72
<211> LENGTH: 20
<212> TYPE: DNA
<213> ORGANISM: Artificial Sequence
<220> FEATURE:
<223> OTHER INFORMATION: ASO

<400> SEQUENCE: 72
gcccgcagtg gccgcagagc                                                    20

<210> SEQ ID NO 73
<211> LENGTH: 20
<212> TYPE: DNA
<213> ORGANISM: Artificial Sequence
<220> FEATURE:
<223> OTHER INFORMATION: ASO

<400> SEQUENCE: 73
gggcatccac caccaccgc                                                     20

<210> SEQ ID NO 74
<211> LENGTH: 20
<212> TYPE: DNA
<213> ORGANISM: Artificial Sequence
<220> FEATURE:
<223> OTHER INFORMATION: ASO

<400> SEQUENCE: 74
ggcgcccacc agggcatcca                                                    20

<210> SEQ ID NO 75
<211> LENGTH: 20
<212> TYPE: DNA
<213> ORGANISM: Artificial Sequence
<220> FEATURE:
<223> OTHER INFORMATION: ASO

<400> SEQUENCE: 75
tgtcctccca cttgggttgc                                                    20
```

<210> SEQ ID NO 76
<211> LENGTH: 20
<212> TYPE: DNA
<213> ORGANISM: Artificial Sequence
<220> FEATURE:
<223> OTHER INFORMATION: ASO

<400> SEQUENCE: 76
tcccctctgg tgccattgct                                               20

<210> SEQ ID NO 77
<211> LENGTH: 20
<212> TYPE: DNA
<213> ORGANISM: Artificial Sequence
<220> FEATURE:
<223> OTHER INFORMATION: ASO

<400> SEQUENCE: 77
gggctcccac agtccctct                                                20

<210> SEQ ID NO 78
<211> LENGTH: 20
<212> TYPE: DNA
<213> ORGANISM: Artificial Sequence
<220> FEATURE:
<223> OTHER INFORMATION: ASO

<400> SEQUENCE: 78
gcagcctcct cctcagctct                                               20

<210> SEQ ID NO 79
<211> LENGTH: 20
<212> TYPE: DNA
<213> ORGANISM: Artificial Sequence
<220> FEATURE:
<223> OTHER INFORMATION: ASO

<400> SEQUENCE: 79
gccatatcct caccctctca                                               20

<210> SEQ ID NO 80
<211> LENGTH: 20
<212> TYPE: DNA
<213> ORGANISM: Artificial Sequence
<220> FEATURE:
<223> OTHER INFORMATION: ASO

<400> SEQUENCE: 80
gggactgctt tctcccttcc                                               20

<210> SEQ ID NO 81
<211> LENGTH: 20
<212> TYPE: DNA
<213> ORGANISM: Artificial Sequence
<220> FEATURE:
<223> OTHER INFORMATION: ASO

<400> SEQUENCE: 81
tgccttgtct ctggcctccc                                               20

<210> SEQ ID NO 82
<211> LENGTH: 20
<212> TYPE: DNA
<213> ORGANISM: Artificial Sequence
<220> FEATURE:

```
<223> OTHER INFORMATION: ASO

<400> SEQUENCE: 82
gcttgtttcc agtcctcagc                                              20

<210> SEQ ID NO 83
<211> LENGTH: 20
<212> TYPE: DNA
<213> ORGANISM: Artificial Sequence
<220> FEATURE:
<223> OTHER INFORMATION: ASO

<400> SEQUENCE: 83
gaccttcctc ccacagtgcc                                              20

<210> SEQ ID NO 84
<211> LENGTH: 20
<212> TYPE: DNA
<213> ORGANISM: Artificial Sequence
<220> FEATURE:
<223> OTHER INFORMATION: ASO

<400> SEQUENCE: 84
gagccaccct cccacacagc                                              20

<210> SEQ ID NO 85
<211> LENGTH: 20
<212> TYPE: DNA
<213> ORGANISM: Artificial Sequence
<220> FEATURE:
<223> OTHER INFORMATION: ASO

<400> SEQUENCE: 85
acagcagtgt ctccttggcc                                              20

<210> SEQ ID NO 86
<211> LENGTH: 20
<212> TYPE: DNA
<213> ORGANISM: Artificial Sequence
<220> FEATURE:
<223> OTHER INFORMATION: ASO

<400> SEQUENCE: 86
cccagtgtcc acatgtctcc                                              20

<210> SEQ ID NO 87
<211> LENGTH: 20
<212> TYPE: DNA
<213> ORGANISM: Artificial Sequence
<220> FEATURE:
<223> OTHER INFORMATION: ASO

<400> SEQUENCE: 87
tctgttgctc ccaccagctt                                              20

<210> SEQ ID NO 88
<211> LENGTH: 20
<212> TYPE: DNA
<213> ORGANISM: Artificial Sequence
<220> FEATURE:
<223> OTHER INFORMATION: ASO

<400> SEQUENCE: 88
gcctcttctg tggaggtggg                                              20
```

```
<210> SEQ ID NO 89
<211> LENGTH: 20
<212> TYPE: DNA
<213> ORGANISM: Artificial Sequence
<220> FEATURE:
<223> OTHER INFORMATION: ASO

<400> SEQUENCE: 89
ccactcacca ccaggttccc                                              20

<210> SEQ ID NO 90
<211> LENGTH: 20
<212> TYPE: DNA
<213> ORGANISM: Artificial Sequence
<220> FEATURE:
<223> OTHER INFORMATION: ASO

<400> SEQUENCE: 90
ggtctcctct gcatttccct                                              20

<210> SEQ ID NO 91
<211> LENGTH: 20
<212> TYPE: DNA
<213> ORGANISM: Artificial Sequence
<220> FEATURE:
<223> OTHER INFORMATION: ASO

<400> SEQUENCE: 91
gccctgcatg ttcctgaggc                                              20

<210> SEQ ID NO 92
<211> LENGTH: 20
<212> TYPE: DNA
<213> ORGANISM: Artificial Sequence
<220> FEATURE:
<223> OTHER INFORMATION: ASO

<400> SEQUENCE: 92
gctggctgtc caacctctcc                                              20

<210> SEQ ID NO 93
<211> LENGTH: 20
<212> TYPE: DNA
<213> ORGANISM: Artificial Sequence
<220> FEATURE:
<223> OTHER INFORMATION: ASO

<400> SEQUENCE: 93
ccagcctcta ccagcccact                                              20

<210> SEQ ID NO 94
<211> LENGTH: 20
<212> TYPE: DNA
<213> ORGANISM: Artificial Sequence
<220> FEATURE:
<223> OTHER INFORMATION: ASO

<400> SEQUENCE: 94
gccctccctc ttatcttacc                                              20

<210> SEQ ID NO 95
<211> LENGTH: 20
<212> TYPE: DNA
<213> ORGANISM: Artificial Sequence
<220> FEATURE:
<223> OTHER INFORMATION: ASO
```

<400> SEQUENCE: 95
gccaccctag ttttcctccc                                              20

<210> SEQ ID NO 96
<211> LENGTH: 20
<212> TYPE: DNA
<213> ORGANISM: Artificial Sequence
<220> FEATURE:
<223> OTHER INFORMATION: ASO

<400> SEQUENCE: 96
ggtgccagcc tgttcagtcc                                              20

<210> SEQ ID NO 97
<211> LENGTH: 20
<212> TYPE: DNA
<213> ORGANISM: Artificial Sequence
<220> FEATURE:
<223> OTHER INFORMATION: ASO

<400> SEQUENCE: 97
gtccacccaa gcccacctcc                                              20

<210> SEQ ID NO 98
<211> LENGTH: 20
<212> TYPE: DNA
<213> ORGANISM: Artificial Sequence
<220> FEATURE:
<223> OTHER INFORMATION: ASO

<400> SEQUENCE: 98
ggaactccct gcccagcctc                                              20

<210> SEQ ID NO 99
<211> LENGTH: 20
<212> TYPE: DNA
<213> ORGANISM: Artificial Sequence
<220> FEATURE:
<223> OTHER INFORMATION: ASO

<400> SEQUENCE: 99
gtctgggtcc tggtggctgt                                              20

<210> SEQ ID NO 100
<211> LENGTH: 20
<212> TYPE: DNA
<213> ORGANISM: Artificial Sequence
<220> FEATURE:
<223> OTHER INFORMATION: ASO

<400> SEQUENCE: 100
gccctgccag tcacactgcc                                              20

<210> SEQ ID NO 101
<211> LENGTH: 20
<212> TYPE: DNA
<213> ORGANISM: Artificial Sequence
<220> FEATURE:
<223> OTHER INFORMATION: ASO

<400> SEQUENCE: 101
ggctgatcct tgccttctgc                                              20

<210> SEQ ID NO 102
<211> LENGTH: 20

```
<212> TYPE: DNA
<213> ORGANISM: Artificial Sequence
<220> FEATURE:
<223> OTHER INFORMATION: ASO

<400> SEQUENCE: 102
ttgctctagg agctgtggct                                            20

<210> SEQ ID NO 103
<211> LENGTH: 20
<212> TYPE: DNA
<213> ORGANISM: Artificial Sequence
<220> FEATURE:
<223> OTHER INFORMATION: ASO

<400> SEQUENCE: 103
agcactcagt gctctctgcc                                            20

<210> SEQ ID NO 104
<211> LENGTH: 20
<212> TYPE: DNA
<213> ORGANISM: Artificial Sequence
<220> FEATURE:
<223> OTHER INFORMATION: ASO

<400> SEQUENCE: 104
gatggtgatg gccagctcag                                            20

<210> SEQ ID NO 105
<211> LENGTH: 20
<212> TYPE: DNA
<213> ORGANISM: Artificial Sequence
<220> FEATURE:
<223> OTHER INFORMATION: ASO

<400> SEQUENCE: 105
ggcctccatc ttgtgatgct                                            20

<210> SEQ ID NO 106
<211> LENGTH: 20
<212> TYPE: DNA
<213> ORGANISM: Artificial Sequence
<220> FEATURE:
<223> OTHER INFORMATION: ASO

<400> SEQUENCE: 106
agggctccga cagagttgcc                                            20

<210> SEQ ID NO 107
<211> LENGTH: 20
<212> TYPE: DNA
<213> ORGANISM: Artificial Sequence
<220> FEATURE:
<223> OTHER INFORMATION: ASO

<400> SEQUENCE: 107
gtcaggcttc caagggctcc                                            20

<210> SEQ ID NO 108
<211> LENGTH: 20
<212> TYPE: DNA
<213> ORGANISM: Artificial Sequence
<220> FEATURE:
<223> OTHER INFORMATION: ASO

<400> SEQUENCE: 108
```
agtcaggctt ccaagggctc                                      20

<210> SEQ ID NO 109
<211> LENGTH: 20
<212> TYPE: DNA
<213> ORGANISM: Artificial Sequence
<220> FEATURE:
<223> OTHER INFORMATION: ASO

<400> SEQUENCE: 109
ggaccacagt caggcttcca                                      20

<210> SEQ ID NO 110
<211> LENGTH: 20
<212> TYPE: DNA
<213> ORGANISM: Artificial Sequence
<220> FEATURE:
<223> OTHER INFORMATION: ASO

<400> SEQUENCE: 110
gtcgggcctg tcgggttaca                                      20

<210> SEQ ID NO 111
<211> LENGTH: 20
<212> TYPE: DNA
<213> ORGANISM: Artificial Sequence
<220> FEATURE:
<223> OTHER INFORMATION: ASO

<400> SEQUENCE: 111
tgtcgggcct gtcgggttac                                      20

<210> SEQ ID NO 112
<211> LENGTH: 20
<212> TYPE: DNA
<213> ORGANISM: Artificial Sequence
<220> FEATURE:
<223> OTHER INFORMATION: ASO

<400> SEQUENCE: 112
ctgtcgggcc tgtcgggtta                                      20

<210> SEQ ID NO 113
<211> LENGTH: 20
<212> TYPE: DNA
<213> ORGANISM: Artificial Sequence
<220> FEATURE:
<223> OTHER INFORMATION: ASO

<400> SEQUENCE: 113
actgtcgggc ctgtcgggtt                                      20

<210> SEQ ID NO 114
<211> LENGTH: 20
<212> TYPE: DNA
<213> ORGANISM: Artificial Sequence
<220> FEATURE:
<223> OTHER INFORMATION: ASO

<400> SEQUENCE: 114
gactgtcggg cctgtcgggt                                      20

<210> SEQ ID NO 115
<211> LENGTH: 20
<212> TYPE: DNA
<213> ORGANISM: Artificial Sequence

```
<220> FEATURE:
<223> OTHER INFORMATION: ASO

<400> SEQUENCE: 115
agactgtcgg gcctgtcggg                                               20

<210> SEQ ID NO 116
<211> LENGTH: 20
<212> TYPE: DNA
<213> ORGANISM: Artificial Sequence
<220> FEATURE:
<223> OTHER INFORMATION: ASO

<400> SEQUENCE: 116
ccccatgtgc cagtgccgta                                               20

<210> SEQ ID NO 117
<211> LENGTH: 20
<212> TYPE: DNA
<213> ORGANISM: Artificial Sequence
<220> FEATURE:
<223> OTHER INFORMATION: ASO

<400> SEQUENCE: 117
cctgggtctc tgagcccctt                                               20

<210> SEQ ID NO 118
<211> LENGTH: 20
<212> TYPE: DNA
<213> ORGANISM: Artificial Sequence
<220> FEATURE:
<223> OTHER INFORMATION: ASO

<400> SEQUENCE: 118
tcctgggtct ctgagcccct                                               20

<210> SEQ ID NO 119
<211> LENGTH: 20
<212> TYPE: DNA
<213> ORGANISM: Artificial Sequence
<220> FEATURE:
<223> OTHER INFORMATION: ASO

<400> SEQUENCE: 119
aagctcctcc tgggtctctg                                               20

<210> SEQ ID NO 120
<211> LENGTH: 20
<212> TYPE: DNA
<213> ORGANISM: Artificial Sequence
<220> FEATURE:
<223> OTHER INFORMATION: ASO

<400> SEQUENCE: 120
gtgggcttct tgttctcctg                                               20

<210> SEQ ID NO 121
<211> LENGTH: 20
<212> TYPE: DNA
<213> ORGANISM: Artificial Sequence
<220> FEATURE:
<223> OTHER INFORMATION: ASO

<400> SEQUENCE: 121
gtagcaggtt ttccgcaggt                                               20
```

```
<210> SEQ ID NO 122
<211> LENGTH: 20
<212> TYPE: DNA
<213> ORGANISM: Artificial Sequence
<220> FEATURE:
<223> OTHER INFORMATION: ASO

<400> SEQUENCE: 122
ggtactagct cctcctgcct                                                   20

<210> SEQ ID NO 123
<211> LENGTH: 20
<212> TYPE: DNA
<213> ORGANISM: Artificial Sequence
<220> FEATURE:
<223> OTHER INFORMATION: ASO

<400> SEQUENCE: 123
catccacctc cagacctccc                                                   20

<210> SEQ ID NO 124
<211> LENGTH: 20
<212> TYPE: DNA
<213> ORGANISM: Artificial Sequence
<220> FEATURE:
<223> OTHER INFORMATION: ASO

<400> SEQUENCE: 124
gcccaagtcc ctcaagcctt                                                   20

<210> SEQ ID NO 125
<211> LENGTH: 20
<212> TYPE: DNA
<213> ORGANISM: Artificial Sequence
<220> FEATURE:
<223> OTHER INFORMATION: ASO

<400> SEQUENCE: 125
ggttccaggt tccacccagc                                                   20

<210> SEQ ID NO 126
<211> LENGTH: 20
<212> TYPE: DNA
<213> ORGANISM: Artificial Sequence
<220> FEATURE:
<223> OTHER INFORMATION: ASO

<400> SEQUENCE: 126
ctgtctcctc cataggtcct                                                   20

<210> SEQ ID NO 127
<211> LENGTH: 20
<212> TYPE: DNA
<213> ORGANISM: Artificial Sequence
<220> FEATURE:
<223> OTHER INFORMATION: ASO

<400> SEQUENCE: 127
ttcctccctg ccttatgggt                                                   20

<210> SEQ ID NO 128
<211> LENGTH: 20
<212> TYPE: DNA
<213> ORGANISM: Artificial Sequence
<220> FEATURE:
<223> OTHER INFORMATION: ASO
```

```
<400> SEQUENCE: 128
gctcctcctt gcttcaggct                                              20

<210> SEQ ID NO 129
<211> LENGTH: 20
<212> TYPE: DNA
<213> ORGANISM: Artificial Sequence
<220> FEATURE:
<223> OTHER INFORMATION: ASO

<400> SEQUENCE: 129
gcatccaggc atctcagtgc                                              20

<210> SEQ ID NO 130
<211> LENGTH: 20
<212> TYPE: DNA
<213> ORGANISM: Artificial Sequence
<220> FEATURE:
<223> OTHER INFORMATION: ASO

<400> SEQUENCE: 130
gccctatgcc tgcctcagtg                                              20

<210> SEQ ID NO 131
<211> LENGTH: 20
<212> TYPE: DNA
<213> ORGANISM: Artificial Sequence
<220> FEATURE:
<223> OTHER INFORMATION: ASO

<400> SEQUENCE: 131
ccacacctgt ctgcctgtgt                                              20

<210> SEQ ID NO 132
<211> LENGTH: 20
<212> TYPE: DNA
<213> ORGANISM: Artificial Sequence
<220> FEATURE:
<223> OTHER INFORMATION: ASO

<400> SEQUENCE: 132
gtgtcctctg cctctctact                                              20

<210> SEQ ID NO 133
<211> LENGTH: 20
<212> TYPE: DNA
<213> ORGANISM: Artificial Sequence
<220> FEATURE:
<223> OTHER INFORMATION: ASO

<400> SEQUENCE: 133
cctgccttct cagagtgcca                                              20

<210> SEQ ID NO 134
<211> LENGTH: 20
<212> TYPE: DNA
<213> ORGANISM: Artificial Sequence
<220> FEATURE:
<223> OTHER INFORMATION: ASO

<400> SEQUENCE: 134
gccctctttc tcaccagacc                                              20

<210> SEQ ID NO 135
```

-continued

```
<210> SEQ ID NO 136
<211> LENGTH: 20
<212> TYPE: DNA
<213> ORGANISM: Artificial Sequence
<220> FEATURE:
<223> OTHER INFORMATION: ASO

<400> SEQUENCE: 135
cccatgtccc tacctcctttt                                              20

<210> SEQ ID NO 136
<211> LENGTH: 20
<212> TYPE: DNA
<213> ORGANISM: Artificial Sequence
<220> FEATURE:
<223> OTHER INFORMATION: ASO

<400> SEQUENCE: 136
gtcccatccc aagtctagcc                                               20

<210> SEQ ID NO 137
<211> LENGTH: 20
<212> TYPE: DNA
<213> ORGANISM: Artificial Sequence
<220> FEATURE:
<223> OTHER INFORMATION: ASO

<400> SEQUENCE: 137
tctttaggtc ctgttgccct                                               20

<210> SEQ ID NO 138
<211> LENGTH: 20
<212> TYPE: DNA
<213> ORGANISM: Artificial Sequence
<220> FEATURE:
<223> OTHER INFORMATION: ASO

<400> SEQUENCE: 138
cccactcctc ccttctttga                                               20

<210> SEQ ID NO 139
<211> LENGTH: 20
<212> TYPE: DNA
<213> ORGANISM: Artificial Sequence
<220> FEATURE:
<223> OTHER INFORMATION: ASO

<400> SEQUENCE: 139
gggctctctt cactctgcct                                               20

<210> SEQ ID NO 140
<211> LENGTH: 20
<212> TYPE: DNA
<213> ORGANISM: Artificial Sequence
<220> FEATURE:
<223> OTHER INFORMATION: ASO

<400> SEQUENCE: 140
gggtcctctc tgttgccact                                               20

<210> SEQ ID NO 141
<211> LENGTH: 20
<212> TYPE: DNA
<213> ORGANISM: Artificial Sequence
<220> FEATURE:
<223> OTHER INFORMATION: ASO

<400> SEQUENCE: 141
```
ctccctagcc ctgcctcttc                                               20

<210> SEQ ID NO 142
<211> LENGTH: 19
<212> TYPE: DNA
<213> ORGANISM: Artificial Sequence
<220> FEATURE:
<223> OTHER INFORMATION: ASO

<400> SEQUENCE: 142
caaaatccag ccagttcca                                                19

<210> SEQ ID NO 143
<211> LENGTH: 19
<212> TYPE: DNA
<213> ORGANISM: Artificial Sequence
<220> FEATURE:
<223> OTHER INFORMATION: ASO

<400> SEQUENCE: 143
tgcaatgtac atgttcacc                                                19

<210> SEQ ID NO 144
<211> LENGTH: 19
<212> TYPE: DNA
<213> ORGANISM: Artificial Sequence
<220> FEATURE:
<223> OTHER INFORMATION: ASO

<400> SEQUENCE: 144
ctgcaatgta catgttcac                                                19

<210> SEQ ID NO 145
<211> LENGTH: 19
<212> TYPE: DNA
<213> ORGANISM: Artificial Sequence
<220> FEATURE:
<223> OTHER INFORMATION: ASO

<400> SEQUENCE: 145
actgcaatgt acatgttca                                                19

<210> SEQ ID NO 146
<211> LENGTH: 19
<212> TYPE: DNA
<213> ORGANISM: Artificial Sequence
<220> FEATURE:
<223> OTHER INFORMATION: ASO

<400> SEQUENCE: 146
tgactgcaat gtacatgtt                                                19

<210> SEQ ID NO 147
<211> LENGTH: 19
<212> TYPE: DNA
<213> ORGANISM: Artificial Sequence
<220> FEATURE:
<223> OTHER INFORMATION: ASO

<400> SEQUENCE: 147
atgactgcaa tgtacatgt                                                19

<210> SEQ ID NO 148
<211> LENGTH: 19
<212> TYPE: DNA

<213> ORGANISM: Artificial Sequence
<220> FEATURE:
<223> OTHER INFORMATION: ASO

<400> SEQUENCE: 148
gtcatttttg ccatgttat                                                   19

<210> SEQ ID NO 149
<211> LENGTH: 19
<212> TYPE: DNA
<213> ORGANISM: Artificial Sequence
<220> FEATURE:
<223> OTHER INFORMATION: ASO

<400> SEQUENCE: 149
tcaaataacc cagaagcct                                                   19

<210> SEQ ID NO 150
<211> LENGTH: 19
<212> TYPE: DNA
<213> ORGANISM: Artificial Sequence
<220> FEATURE:
<223> OTHER INFORMATION: ASO

<400> SEQUENCE: 150
ttcaaataac ccagaagcc                                                   19

<210> SEQ ID NO 151
<211> LENGTH: 19
<212> TYPE: DNA
<213> ORGANISM: Artificial Sequence
<220> FEATURE:
<223> OTHER INFORMATION: ASO

<400> SEQUENCE: 151
tttcaaataa cccagaagc                                                   19

<210> SEQ ID NO 152
<211> LENGTH: 19
<212> TYPE: DNA
<213> ORGANISM: Artificial Sequence
<220> FEATURE:
<223> OTHER INFORMATION: ASO

<400> SEQUENCE: 152
aaaatccagc cagttccaa                                                   19

<210> SEQ ID NO 153
<211> LENGTH: 19
<212> TYPE: DNA
<213> ORGANISM: Artificial Sequence
<220> FEATURE:
<223> OTHER INFORMATION: ASO

<400> SEQUENCE: 153
aggcctggga tcacagaaa                                                   19

<210> SEQ ID NO 154
<211> LENGTH: 19
<212> TYPE: DNA
<213> ORGANISM: Artificial Sequence
<220> FEATURE:
<223> OTHER INFORMATION: ASO

<400> SEQUENCE: 154
caggcctggg atcacagaa                                                   19

<210> SEQ ID NO 155
<211> LENGTH: 19
<212> TYPE: DNA
<213> ORGANISM: Artificial Sequence
<220> FEATURE:
<223> OTHER INFORMATION: ASO

<400> SEQUENCE: 155
tcaggcctgg gatcacaga                                            19

<210> SEQ ID NO 156
<211> LENGTH: 19
<212> TYPE: DNA
<213> ORGANISM: Artificial Sequence
<220> FEATURE:
<223> OTHER INFORMATION: ASO

<400> SEQUENCE: 156
ttcaggcctg ggatcacag                                            19

<210> SEQ ID NO 157
<211> LENGTH: 19
<212> TYPE: DNA
<213> ORGANISM: Artificial Sequence
<220> FEATURE:
<223> OTHER INFORMATION: ASO

<400> SEQUENCE: 157
cttcaggcct gggatcaca                                            19

<210> SEQ ID NO 158
<211> LENGTH: 19
<212> TYPE: DNA
<213> ORGANISM: Artificial Sequence
<220> FEATURE:
<223> OTHER INFORMATION: ASO

<400> SEQUENCE: 158
tgctctgtga ataaatgct                                            19

<210> SEQ ID NO 159
<211> LENGTH: 19
<212> TYPE: DNA
<213> ORGANISM: Artificial Sequence
<220> FEATURE:
<223> OTHER INFORMATION: ASO

<400> SEQUENCE: 159
taatttggca tctgtctttt                                           19

<210> SEQ ID NO 160
<211> LENGTH: 19
<212> TYPE: DNA
<213> ORGANISM: Artificial Sequence
<220> FEATURE:
<223> OTHER INFORMATION: ASO

<400> SEQUENCE: 160
tcagataacc cagaagcct                                            19

<210> SEQ ID NO 161
<211> LENGTH: 19
<212> TYPE: DNA
<213> ORGANISM: Artificial Sequence
<220> FEATURE:

```
<223> OTHER INFORMATION: ASO

<400> SEQUENCE: 161
ttcagataac ccagaagcc                                                19

<210> SEQ ID NO 162
<211> LENGTH: 19
<212> TYPE: DNA
<213> ORGANISM: Artificial Sequence
<220> FEATURE:
<223> OTHER INFORMATION: ASO

<400> SEQUENCE: 162
tttcagataa cccagaagc                                                19

<210> SEQ ID NO 163
<211> LENGTH: 19
<212> TYPE: DNA
<213> ORGANISM: Artificial Sequence
<220> FEATURE:
<223> OTHER INFORMATION: ASO

<400> SEQUENCE: 163
ggatgatgaa tagatggaa                                                19

<210> SEQ ID NO 164
<211> LENGTH: 19
<212> TYPE: DNA
<213> ORGANISM: Artificial Sequence
<220> FEATURE:
<223> OTHER INFORMATION: ASO

<400> SEQUENCE: 164
caaaatccag ccagttcca                                                19

<210> SEQ ID NO 165
<211> LENGTH: 20
<212> TYPE: DNA
<213> ORGANISM: Artificial Sequence
<220> FEATURE:
<223> OTHER INFORMATION: Control

<400> SEQUENCE: 165
gccauaatcc gggttucugc                                               20
```

THERAPEUTIC COMPOSITIONS FOR TREATING PAIN VIA MULTIPLE TARGETS

SEQUENCE LISTING

This application contains a sequence listing which has been submitted in ASCII format via EFS-Web and is hereby incorporated by reference in its entirety. The ASCII-formatted sequence listing, created on Dec. 13, 2021, is named QSTA-029-01US-Seqs.txt, and is 29,435 bytes in size.

TECHNICAL FIELD

The disclosure relates to non-opioid therapeutic compositions for treating pain.

BACKGROUND

In the United States, the Center for Disease Control estimates that as many as 100 million people suffer from chronic pain. One prevalent approach to the treatment of pain involves the use of opioids. Although opioid drugs are highly effective treatments for pain, the abuse of those addictive drugs is understood to be an epidemic problem. Nevertheless, there are many common medical conditions that are painful to experience and live with.

One common medical condition that often induces severe chronic pain is osteoarthritis. Osteoarthritis occurs when the cartilage in joints breaks down or wears away, eventually leading to exposed bone on the joint surfaces that rub together and can fragment or splinter. Many people who suffer from osteoarthritis are familiar with the enduring pain that this condition brings. Another common medical condition that may cause severe chronic pain is cancer. The American Cancer Society attributes cancer pain to the cancer itself, not merely to an inflammatory response to the cancer. Research indicates that cancer cells themselves drive hypersensitivity of sensory neurons. Thus, not only can a cancer manifest as a tumor, or spread throughout the body, but the cancer itself can be a direct cause of severe pain.

There are various approaches to treating pain, but each is associated with specific limitations. Over-the-counter non-steroidal anti-inflammatory drugs (NSAIDs) may lack the necessary efficacy to treat certain forms of pain. In addition, some people become non-responsive to NSAIDs or cannot tolerate adverse effects on the digestive system and kidney function. Opioids are understood to be effective for treating pain, but come with a steep human and societal cost and may lose efficacy over time due to development of tolerance. Opioids are addictive narcotics and are well-understood to be implicated in abuse, diversion, and even fraud and criminal activity. Further serious drawbacks of NSAID and opioid treatment include a high death toll.

SUMMARY

The invention provides therapeutic compositions useful to treat pain that do not require or involve opioids. The compositions include short nucleic acids, or oligonucleotides, that prevent the synthesis of proteins involved in the perception of pain. Specifically, certain neurons operate as "pain-sensing" nerves, or nociceptors. Those pain-sensing neurons have proteins that function as voltage-gated sodium channels. When stimulation of the nerve endings exceeds a threshold voltage (V), the nociceptor neurons conduct sodium ions (Na+) across the cell membrane, which can cause the neuron to depolarize in a regenerative fashion leading to "firing" of propagating electrical signals that underlie the sensation of pain. Compositions of the invention include oligonucleotides that bind to the messenger RNA (mRNA) or precursor mRNA (pre-mRNA) used in making those sodium channel proteins that enable pain sensation. The invention includes the identification of numerous specific validated targets within those RNAs. The oligonucleotides prevent those proteins from being made, which decreases the sensitivity or activity of those pain-sensing neurons. Because activity of the pain sensing neurons is decreased, the patient experiences far less pain. The compositions do not need to include any opioids or other narcotics, and thus are not habit-forming. The compositions may be used in combination with opioids to reduce effective doses of opioids. The compositions thus provide long-term pain relief by downregulating sodium channels in pain-sensing neurons.

There are nine families of voltage-gated sodium channels in humans, named NaV1.1 through NaV1.9. Of those nine proteins, NaV1.7, NaV1.8, and NaV1.9 are expressed in nociceptor dorsal root ganglion (DRG) neurons and contribute to the perception of pain.

Oligonucleotides of the disclosure are designed to bind to certain targets in the RNAs used in synthesis of the NaV1.7, NaV1.8, and NaV1.9 proteins. Binding of the oligonucleotides prevents protein synthesis and downregulates expression of the corresponding NaV channel. Specifically, the oligonucleotides have a sequence that is substantially or entirely complementary to one of the identified targets on a NaV channel pre-mRNA or mRNA. That is, the oligonucleotide is antisense to the identified target. When the antisense oligonucleotide (ASO) hybridizes to its target RNA, they form a double-stranded ASO:RNA duplex that recruits an enzyme (RNase H) that degrades a portion of the double-stranded duplex. Degrading the ASO:RNA duplex depletes the neuron of NaV channel mRNA, which decreases the amount of NaV channel synthesized by the cell. Downregulating NaV channel expression interferes with the ability of the neuron to contribute to the sensation of pain.

Thus, when a composition that includes oligonucleotides that are antisense to the identified targets in NaV1.7, NaV1.8, or NaV1.9 pre-mRNA or mRNA is administered to a patient, that patient will have a diminished experience of pain. Accordingly, compositions of the disclosure are useful to treat pain in patients without requiring the use of opioids and may also minimize or lead to lower use of opioids.

In certain aspects, the disclosure provides a composition for treating pain. The composition includes an oligonucleotide that hybridizes to a pre-mRNA or mRNA encoding a sodium channel protein along a segment of that RNA that is at least about 75% complementary to one of SEQ ID NOs: 1-141 to thereby prevent translation of the RNA into the sodium channel protein. The oligonucleotide may hybridize to, and knockdown expression of, one or more of NaV1.7, NaV1.8, and NaV1.9 pre-mRNA or mRNA. Preferably, a sequence of bases in the oligonucleotide has at least 80% identity to one of SEQ ID NOs: 1-141. For example, the sequence of bases in the oligonucleotide may be at least 90% or 95% identical to one of SEQ ID NOs: 1-101, and the oligonucleotide may hybridize to, and induce RNase H cleavage of, either NaV1.7 or NaV1.8 pre-mRNA or mRNA. The composition may include a plurality of therapeutic oligonucleotides each having a base sequence at least 80, 90, 95, or 100% identical to one of SEQ ID NOs: 1-141.

Therapeutic oligonucleotides of the disclosure may have a gapmer structure that includes a central DNA segment flanked by modified RNA wings. Such a therapeutic oligonucleotide may include two wings flanking a central region of DNA bases (e.g., about 8 to 10 DNA bases). Preferably at least one end of the oligonucleotide comprises modified RNA bases, e.g., any number or any combination of 2'-O-methoxyethyl RNA ("2'-MOE") and/or 2'-O-methyl RNA ("2' O-Me"). In addition, compositions of the invention may be designed to target an exon-exon junction in order to differentially target cytoplasmic versus nuclear mRNA. Thus, ASOs of the invention can be designed to interact with RNA prior to or after splicing, adding specificity and versatility to the compositions.

The therapeutic oligonucleotide may be provided in a solution or carrier formulated for intrathecal injection, preferably about 3 to 4 times per year. The oligonucleotide may be of any suitable length, e.g., at least about 13 bases, preferably between about 15 and 25 bases. The oligonucleotide may have phosphorothioate bonds in the backbone. In preferred embodiments, the oligonucleotide has a base sequence that has been screened and determined to not meet a threshold match for any long, non-coding RNA or other off-target sequences or transcripts in humans. The oligonucleotide may have a base sequence with 0 mismatches to a homologous segment in a non-human primate genome and no more than about 5 mismatches in a homologous segment in a rodent genome.

When the composition is delivered to dorsal root ganglion (DRG) neurons in vitro, the DRG neurons exhibit a dose-dependent knockdown of NaV1.7, NaV1.8, or NaV1.9. The oligonucleotide may be a gapmer having a base sequence with at least a 90% match to one of SEQ ID NO: 1-141, with bases linked by phosphorothioate linkages. The linkages may be all phosphorothioate or a mixture of phosphorothioate and phosphodiester bonds. The oligonucleotide may further have a central 10 DNA bases flanked by a 5' wing and a 3' wing, the 5' wing and the 3' wing each comprising five consecutive 2' modified RNA bases. Preferably, the oligonucleotide has a base sequence matching one of SEQ ID NO: 1-141, with bases linked by phosphorothioate linkages, and a structure having central DNA bases flanked by a 5' wing and a 3' wing. The number of RNA bases in the wings and DNA bases in the central segment may be 5-10-5 or 4-12-4, or a similar suitable pattern. The 5' wing and the 3' wing may each include several 2'-MOE RNA bases. For example, the oligonucleotide may have 5 consecutive 2'-MOE RNA bases in each wing with a central 10 DNA bases (a "5-10-5" structure), with phosphorothioate linkages throughout the central DNA segment and a mixture of phosphorothioate and phosphodiester bonds in the wings.

In combination embodiments, the invention provides compositions that include a plurality of copies of a plurality of distinct therapeutic gapmers, each according to the descriptions above, in a suitable formulation or carrier.

Preferably, an oligonucleotide of the disclosure exhibits at least 25% better NaV knockdown than a control gapmer (e.g., in an assay using DRG neurons in vitro, wherein the control gapmer consists of GCCAUAATCCGGGT-TUCUGC (SEQ ID NO: 165) linked only by phosphorothioate linkages and further comprising a central 10 DNA bases flanked by a 5' wing of five consecutive 2'-MOE RNA bases and 3' wing of five consecutive 2'-MOE RNA bases).

Aspects of the disclosure provide a use of an antisense oligonucleotide (ASO) for the manufacture of a medicament for treating pain in a patient. In the use, the ASO has at least about 75% identity with one of SEQ ID NOs: 1-141, and more preferably at least 90% identity, e.g., 95% or 100% identity. Preferred embodiments use an ASO that is between about 15 and 25 bases in length, preferably between about 18 and 22, or between about 19 and 21 (inclusive). In general, reference to "an ASO" includes numerous copies of substantially identical molecules. Accordingly, "an ASO" may be any number, e.g., hundreds of thousands, or millions, of copies of the indicated ASO. In preferred embodiments, the ASO is 20 bases in length and has the sequence of one of SEQ ID NOs: 1-141 and is used in the manufacture of a medicament for the treatment of pain. The ASO may be provided in any suitable format such as, for example, lyophilized in a tube or in solution in a tube, such as a microcentrifuge tube or a test tube. Preferred embodiments of the use target NaV1.7 and/or NaV1.8. One or more (e.g., two, three, four, or five, or more) ASOs may be used in manufacture of the medicament. The one or more ASOs may hybridize to a target in a NaV1.7 or a NaV1.8 pre-mRNA or mRNA. In certain embodiments of the use, a sequence of bases in the ASO is at least 90% identical to one of SEQ ID NOs: 1-101. In embodiments, an ASO may have a gapmer structure with a central DNA segment flanked by RNA wings, e.g., a central region of 10 DNA bases with 5 modified RNA bases on both sides of the central region. Each modified RNA base may be 2'-MOE. Preferably a backbone of the ASO has a plurality of phosphorothioate bonds, e.g. most or all of the sugar linkages may be phosphorothioate in the use embodiments. The corresponding medicament may be formulated for intrathecal delivery. Accordingly, the ASO may initially be in a form suitable for mixing into a formulation suitable for introduction by injection or a pump. For example, the ASO (thousands or millions or more of copies of one ASO) may be lyophilized in a tube or in solution at a known molality or concentration. The ASO may be dissolved or diluted into a pharmaceutically acceptable composition in which a carrier, such as a solvent and/or excipient, includes the ASO and may be loaded in an IV bag, syringe, or pump. The medicament may be made using more than one ASO, e.g., any combination of 2, 3, 4, or 5, or more. Bases in compositions of the invention may be modified or wobble bases may be used in order to increase the breadth and effectiveness of compositions of the invention. In one example, ASOs for use in the invention may contain methylated bases (e.g., 5-methylcytosine, 5-methyluracil (thymine) and others).

Compositions of the invention may be formulated to accommodate serial dosing. For example, formulations may provide dosages to be administered at two or more separate times and, optionally, with two or more different ASOs, in order to take advantage of optimal therapeutic windows and to avoid potential competition between ASOs. In addition, compositions of the invention, whether administered serially or not, may interact with more than one target, depending on the composition of the ASOs involved. For example, ASOs may comprise targeted mismatches that allow interaction with multiple targets (both within and across mRNA and pre-mRNA species), thus allowing the associated treatment to impact more than one channel.

DETAILED DESCRIPTION

Figure 1:
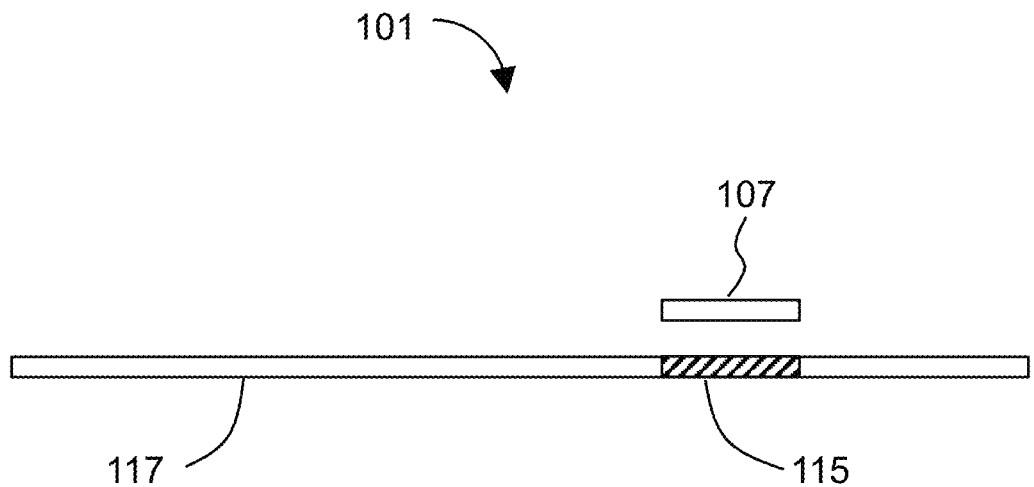
FIG. 1 shows a composition for treating pain.

FIG. 1 shows a composition 101 for treating pain. The composition 101 includes an oligonucleotide 107 that hybridizes to a target segment 115 in an mRNA 117 or a pre-mRNA. The mRNA 117 encodes a sodium channel protein. The segment 115 of the mRNA 117 that includes the target is at least about 75% complementary to one of SEQ ID NOs: 1-141. Hybridization of the oligonucleotide 107 to the segment 115 of the mRNA 117 prevents translation of the mRNA into the sodium channel protein. The oligonucleotide 107 may hybridize to, and knockdown expression of, one or more of NaV1.7, NaV1.8, and NaV1.9 pre-mRNA or mRNA. Preferably, a sequence of bases in the oligonucleotide has at least 80% identity to one of SEQ ID NOs: 1-141, and more preferably at least 90% identity.

In certain embodiments, a sequence of bases in the oligonucleotide is at least 90% identical to one of SEQ ID NOs: 1-101, wherein the oligonucleotide can hybridize to, and induce RNase H cleavage of, either NaV1.7 mRNA or NaV1.8 mRNA.

The oligonucleotide 107 hybridizes to the segment 115 in the mRNA 117 because the oligonucleotide 107 is substantially or entirely antisense to the target segment 115 of the mRNA 117. In that sense, the composition includes an antisense oligonucleotide (ASO). Compositions 101 include ASOs that bind to target RNA with base pair complementarity and exert various effects, based on the ASO chemical structure and design. Various mechanisms, commonly employed in preclinical models of neurological disease and human clinical trial development, may be employed. Those mechanisms include: RNA target degradation via recruitment of the RNase H enzyme; alternative splicing modification to include or exclude exons, and miRNA inhibition to inhibit miRNA binding to its target.

Preferred embodiments of the disclosure include ASOs that hybridize to voltage gated sodium channel (NaV channel) pre-mRNA or mRNA and recruit the RNase H enzyme. The RNase H enzyme cleaves the NaV channel RNA, which downregulates expression of the NaV channel protein. Thus, oligonucleotide 107 of the disclosure address NaV channels as targets for pain therapy. The disclosure builds on the insights that clinical and preclinical data support the use of small molecule NaV blockers for pain therapy. For example, IV lidocaine and lidocaine patches have exhibited pain relief effects, which suggest that blocking synthesis of lidocaine's target may provide similar effects. In fact, numerous agents used for neuropathic pain such as tricyclics and selective serotonin reuptake inhibitors have multiple mechanisms of action, but share ability to block NaV channels. The sodium channels NaV1.7, NaV1.8, and NaV1.9 have been implicated in pain. Those proteins provide a genetic link to pain phenotypes. For example, NaV1.7 loss-of-function has been linked to congenital insensitivity to pain (replicated in mouse models). Additionally, NaV1.7 and NaV1.8 gain-of-function have both been linked to excessive pain disorders. Moreover, NaV1.9 gain-of function is linked to neuropathy with indifference to pain. The genetic insights provide rationales for selectively targeting NaV1.7 and NaV1.8 and NaV1.9. Compositions that include anti-NaV ASOs may be administered to a subject to treat or diminish pain. It may be found that anti-NaV ASOs offer benefits over other approaches such as lidocaine because anti-NaV ASOs may be state independent and subtype selective.

Thus, the disclosure provides a use of an antisense oligonucleotide (ASO) for the manufacture of a medicament for treating pain in a patient. In the use, the ASO has at least about 75% identity with one of SEQ ID NOs: 1-141, and more preferably at least 90% identity, e.g., 95% or greater identity. Preferred embodiments use an ASO that is between about 15 and 25 bases in length, preferably between about 18 and 22 (inclusive). In general, reference to "an ASO" includes numerous copies of substantially identical molecules. Accordingly, "an ASO" may be more than hundreds of thousands or millions of copies of the defined ASO. In preferred embodiments, the ASO is 20 bases in length and has the sequence of one of SEQ ID NOs: 1-141 and is used in the manufacture of a medicament for the treatment of pain. The ASO may be provided in any suitable format such as, for example, lyophilized in a tube or in solution in a tube, such as a microcentrifuge tube or a test tube. Preferred embodiments of the use target NaV1.7 and/or NaV1.8. One or more (e.g., two, three, four, or five, or more) ASOs may be used in manufacture of the medicament. The one or more ASOs may hybridize to a target in a NaV1.7 or a NaV1.8 mRNA. In certain embodiments of the use, a sequence of bases in the ASO is at least 90% identical to one of SEQ ID NOs: 1-101. In embodiments of the use, an ASO may have a gapmer structure with a central DNA segment flanked by RNA wings, e.g., a central region of 10 DNA bases with 5 modified RNA bases on both sides of the central region. Each modified RNA base may be 2'-MOE RNA, 2'-O-Me RNA, or other suitable sugar. Preferably a backbone of the ASO has a plurality of phosphorothioate bonds, either exclusively or also including phosphodiester linkages, e.g., most or all of the sugar linkages may be phosphorothioate in the use embodiments. The medicament may be formulated for intrathecal (IT) delivery. Accordingly, the ASO may initially be in a form suitable for mixing into a formulation suitable for introduction into an intrathecal pump. For example, the ASO (thousands or millions or more of copies of one ASO) may be lyophilized in a tube or in solution at a known molality of concentration. The ASO may be dissolved or diluted into a pharmaceutically acceptable composition in which a carrier, such as a solvent or excipient, includes the ASO and may be loaded in an IV bag, syringe, or intrathecal pump. The medicament may be made using more than one ASO, e.g., any combination of 2, 3, 4, or 5, or more.

Any ASO(s) described in the use embodiment may be included in a composition of the disclosure. Preferred embodiments of compositions of the disclosure include one or a plurality of therapeutic oligonucleotides each having a base sequence at least 80% identical to one of SEQ ID NOs: 1-141, wherein each of the therapeutic oligonucleotides has a gapmer structure that comprises a central DNA segment flanked by modified RNA wings, wherein the plurality of therapeutic oligonucleotides are provided in a solution or carrier formulated for intrathecal injection.

Figure 2:
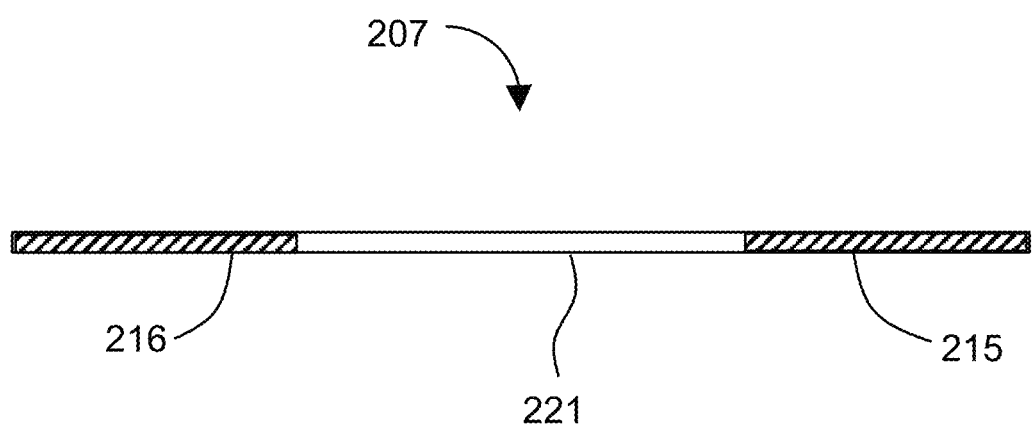
FIG. 2 shows an oligonucleotide with a gapmer structure.

FIG. 2 shows an oligonucleotide 207 with a gapmer structure. The oligonucleotide 207 includes two wings (first wing 215 and second wing 216) flanking a central region 221 of about 10 DNA bases. In preferred embodiments, the wings 215, 216 are all or predominantly RNA bases whereas the central region 221 is all or predominantly DNA bases. Preferably, the wings are all RNA bases (modified or unmodified) and the central region is all DNA bases. In some embodiments, each wing consists of 5 RNA bases, all or most of which are modified RNA bases, e.g., in which each modified RNA base is selected from the group consisting of 2'-O-methoxyethyl RNA and 2'-O-methyl RNA. A modified RNA base may include a substitution on a 2' hydroxyl group of a ribose sugar.

Figure 3:
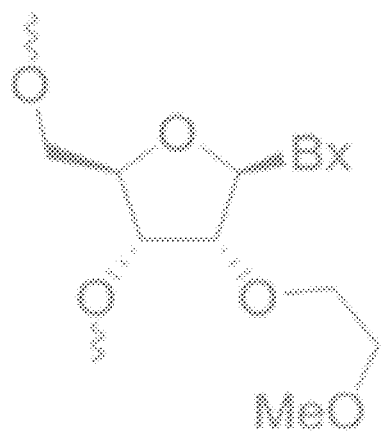
FIG. 3 shows a 2'-O-Methoxyethyl (MOE) modified ribose sugar.

FIG. 3 shows a 2'-O-Methoxyethyl ("2'-MOE") modified sugar that may be included in an RNA base.

The oligonucleotide 207 preferably includes at least about 15 bases, and may include between about 15 about 25 bases. In some embodiments, the oligonucleotide 207 has a backbone comprising a plurality of phosphorothioate bonds.

Figure 4:
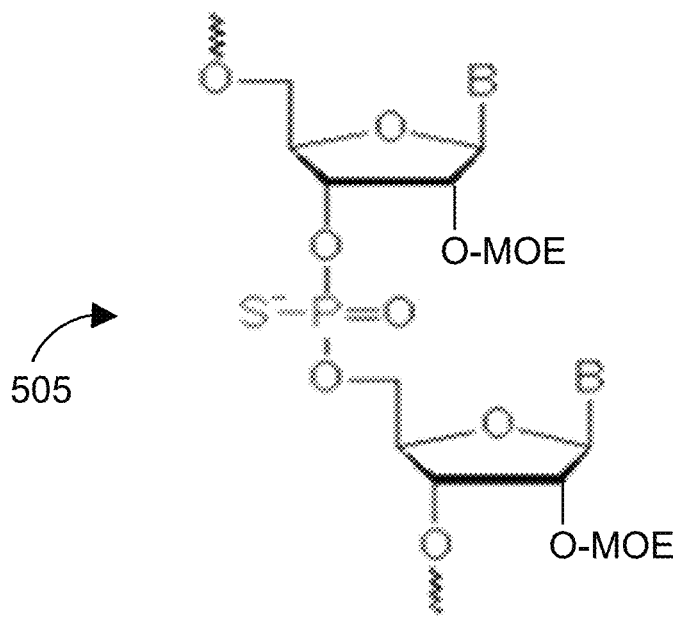
FIG. 4 shows a phosphorothioate bond in a segment of DNA.

FIG. 4 shows a phosphorothioate bond 505 within the backbone of a segment of DNA, such as the central region 221 of the oligonucleotide 207. The oligonucleotide 207 may include one or any number of the phosphorothioate bonds 505. For example, every backbone linkage within the oligonucleotide 207 may be phosphorothioate, or most, or about half may be.

The composition 101 may be formulated for delivery. Accordingly, the oligonucleotide 107 may initially be in a form suitable for mixing into a formulation suitable for introduction into a syringe, bag, or injection pump. For example, the oligonucleotide 107 (thousands or millions or more of copies of one oligonucleotide 107) may be lyophilized in a tube or in solution at a known molality of concentration. The oligonucleotide 107 may be dissolved or diluted into a pharmaceutically acceptable composition in which a carrier, such as a solvent or excipient, includes the oligonucleotide 107 and may be loaded in an IV bag, syringe, or intrathecal pump. As described, the composition 101 includes at least one oligonucleotide 107 with a sequence that is defined by comparison to one of SEQ ID NO: 1-141. Thus, compositions of the disclosure are defined and illustrated by the identified targets.

Specifically, the oligonucleotide 107 hybridizes to an mRNA encoding a sodium channel protein along a segment of the mRNA that is at least about 75% complementary to one of SEQ ID NOs: 1-141 to thereby prevent translation of the mRNA into the sodium channel protein. This is accomplished where the oligonucleotide has at least about 75% identity to one of SEQ ID Nos: 1-141, preferably at least about 90% or 95% identity. In certain embodiments, the oligonucleotide has the sequence of one of SEQ ID Nos: 1-141, although one of skill in the art will understand that oligonucleotides with 90 or preferably 95% identity to a complementary target will still tend to hybridize in a sequence-specific manner to the target. Forming a double stranded structure is energetically favorable enough through Watson-Crick base pairing and base stacking that the double stranded structure can tolerate approximately about 1 mismatched base pair every ten or so. Accordingly, under moderately stringent physiological conditions in a DRG neuron, 95% identity should be effective, especially where an oligonucleotide has a gapmer structure with at least a few modified RNA bases or phosphorothioate backbone linkages to protect the oligonucleotide from enzymatic degradation.

In fact, a feature and benefit of compositions of the disclosure is that the targets (SEQ ID Nos: 1-141) have been screened to rule out sequences for which the complement is present in molecules other than sodium channel transcripts. For example, the sequences have been screened against databases of RNA transcripts including long, non-coding RNA (lncRNA), and initial sequences that matched non-target sequences were excluded. Thus, ASOs with sequences of SEQ ID Nos. 1-141 when administered to a patient should have a minimized chance of hybridizing to non-target sequences. Accordingly, in preferred embodiments, the oligonucleotide 107 has a base sequence that has been screened and determined to not meet a threshold match for any off-target coding or long, non-coding RNA in humans. A composition or use that meets the criteria stated above should not bind to off-target material such as lncRNA in vivo, as the included sequences have been screened against a database of lncRNA. Sequences of the disclosure have been screened for target specificity. Preferably, the oligonucleotide 107 has a base sequence with 0 mis-matches to a homologous segment in a human or non-human primate genome and no more than about 5 mismatches in a homologous segment in a rodent genome. When the composition is delivered to a dorsal root ganglion (DRG) neuron in vitro, the DRG exhibits a dose-dependent knockdown of NaV1.7, NaV1.8, or NaV1.9.

Figure 5:
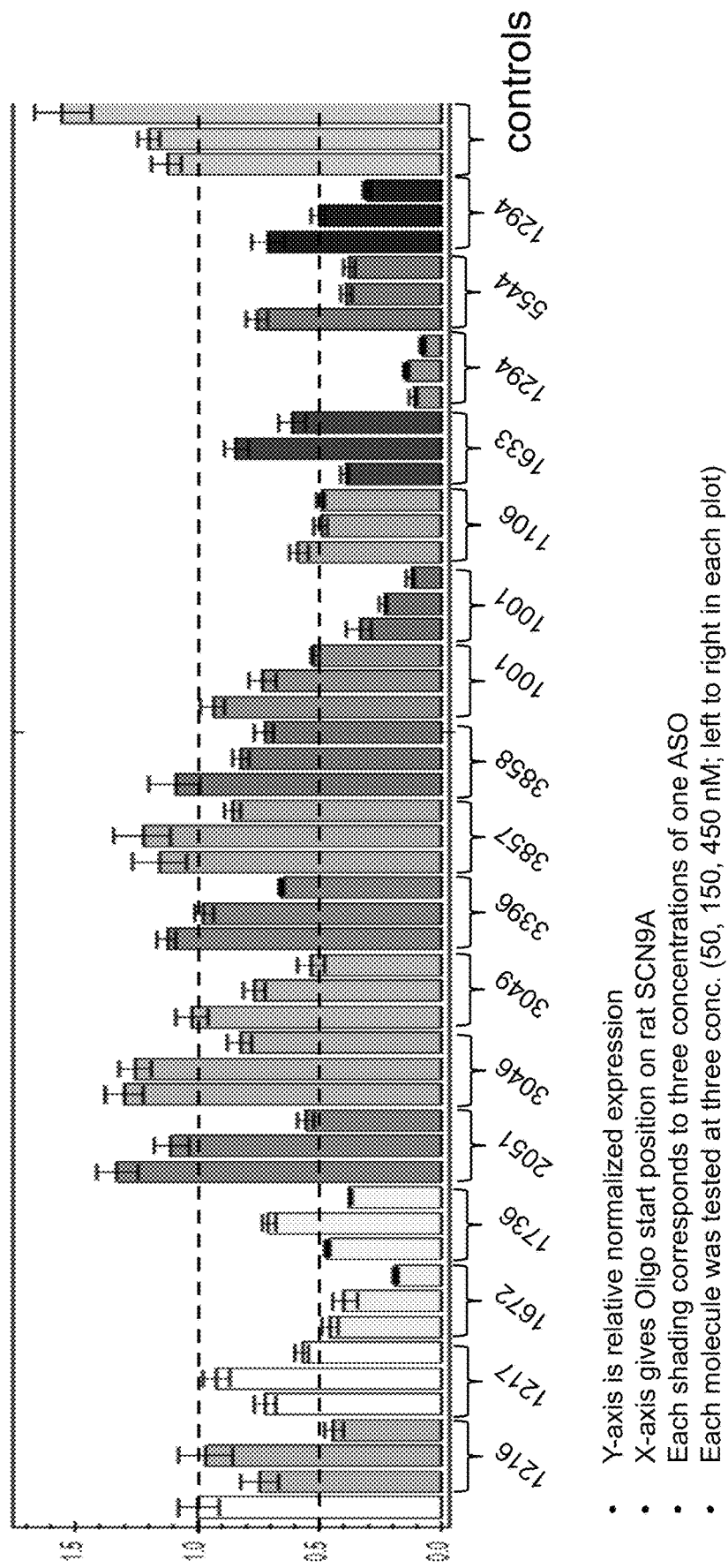
FIG. 5 gives results of a qPCR assay for knockdown of NaV1.7 by 17 different ASOs.

FIG. 5 gives results of a qPCR assay for knockdown of NaV1.7 in rats by 17 different ASOs (at 3 concentrations each) designed according to embodiments of the disclosure (20 bases, 10 base DNA central region flanked by RNA wings with 2'-O modified RNA and phosphorothioate linkages through ASO). Along the bottom of the figure, the "start location" is given, i.e., position within the rat SCN9A mRNA. The right most 3 bars show the expression levels when only controls are administered. All 17 ASOs decreased NaV1.7 expression, relative to controls, for at least the highest concentration. The strongest knockdown was exhibited for the ASO specific to a 20 base target beginning at position 1294. The graph gives results for 17 ASOs, 3 concentrations, applied at DIVE, using gymnotic delivery, with expression levels normalized to GAPDH. The graph shows that a composition 101 of the disclosure exhibits dose-dependent knockdown of NaV1.7.

Because nucleic acid hybridization has some tolerance for mis-matches, it may be found that an oligonucleotide 107 with a base sequence that is at least a 90% match to one of SEQ ID NO: 1-141, with bases linked only by phosphorothioate linkages, and in which the oligonucleotide 107 has a central segment of DNA bases flanked by a 5' wing and a 3' wing (e.g., a 5-10-5 structure in which the 5' wing and the 3' wing each comprise five consecutive 2' modified RNA bases flanking 10 DNA bases, or a 4-12-4 structure, or similar) exhibits dose-dependent knockdown according to the pattern shown in the chart. In some embodiments, the oligonucleotide 107 specifically has a base sequence matching one of SEQ ID NO: 1-141 (more preferably one of SEQ ID NO: 1-101), with bases linked by phosphorothioate linkages (optionally with some phosphodiester linkages in the wings), in which the oligonucleotide 107 has a central 10 DNA bases flanked by a 5' wing and a 3' wing, and in which the 5' wing and the 3' wing each include five consecutive 2' MOE RNA bases.

Figure 6:
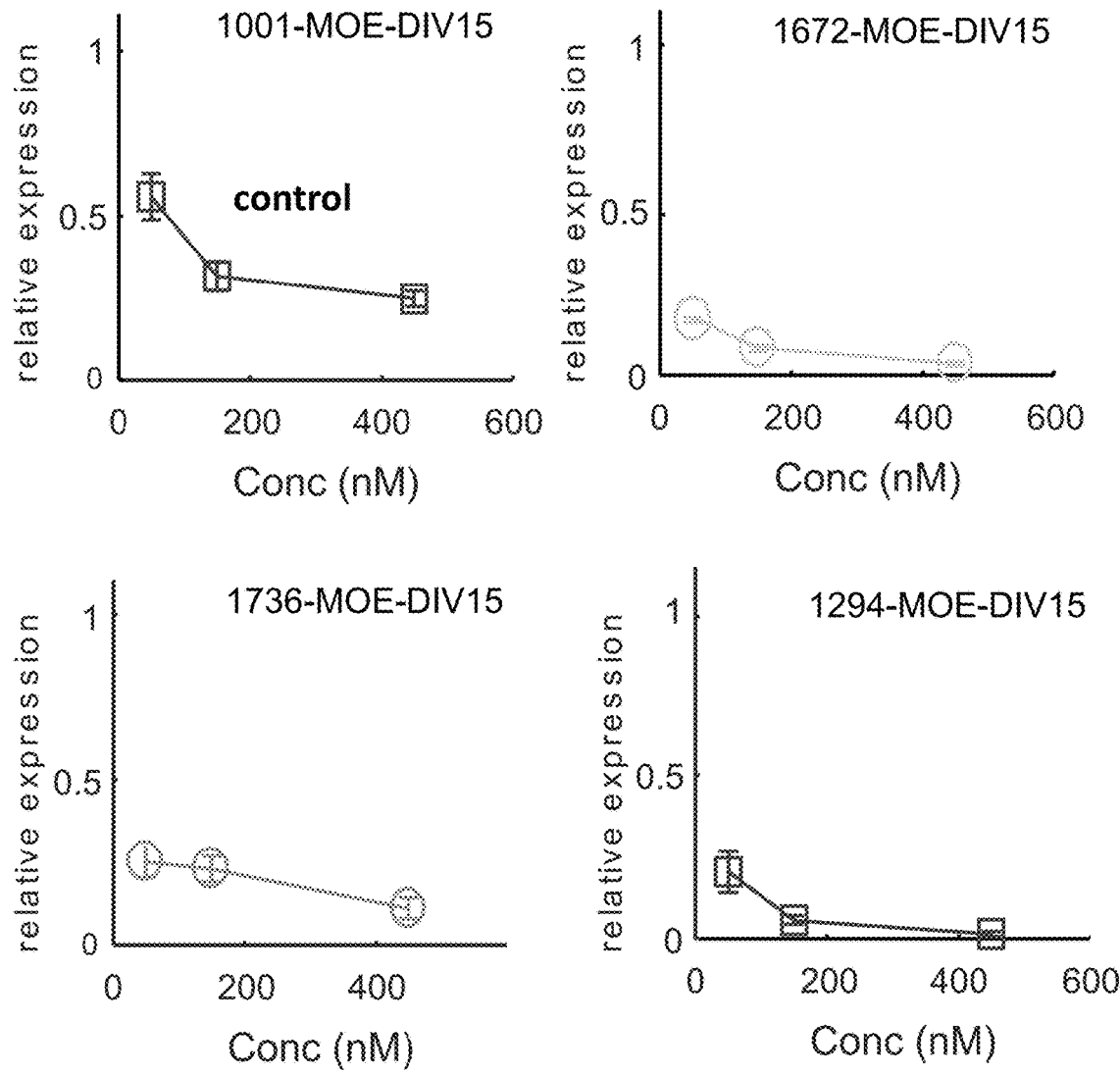
FIG. 6 shows effects of NaV1.7-targeting ASOs compared to a control.

FIG. 6 shows NaV1.7-targeting ASOs effect on mRNA expression at DIV14 in rat DRG neurons compared to a control. It is noted that a composition 101 of the disclosure may include a plurality of copies of a plurality of distinct therapeutic gapmers of one of the preceding claims in a carrier formulated for intrathecal administration. Preferably, any one or more of the oligonucleotides 107 exhibits at least 25% better NaV knockdown than a control gapmer in an assay using DRGs in vitro, where the candidate oligonucleotides and the controls are linked mostly or only by phosphorothioate linkages and include a central segment of DNA bases flanked by a 5' wing of 2'-MOE RNA bases and 3' wing of 2'-MOE RNA bases.

Because these compositions are effective at knocking down expression of sodium channels, the compositions of the disclosure may be used to treat patient populations that experience severe intractable pain. Methods of the disclosure include administering to a patient in need thereof any composition of the disclosure to thereby treat or alleviate cancer pain (e.g., from metastatic bone cancer) or neuropathic pain (e.g., small fiber neuropathy associated with gain-of-function NaV mutations), or other populations. Methods of the disclosure may be used to target any NaV channel as a primary target and may additionally include oligos for a secondary target. For example, the primary target may be NaV1.7 (with oligos having substantial identity to one or more of SEQ ID Nos: 1-53) and secondary target may be NaV1.8 and/or NaV1.9 (with oligos having substantial identity to one or more of SEQ ID Nos: 54-101 and/or SEQ ID Nos: 102-141, respectively).

Figure 7:
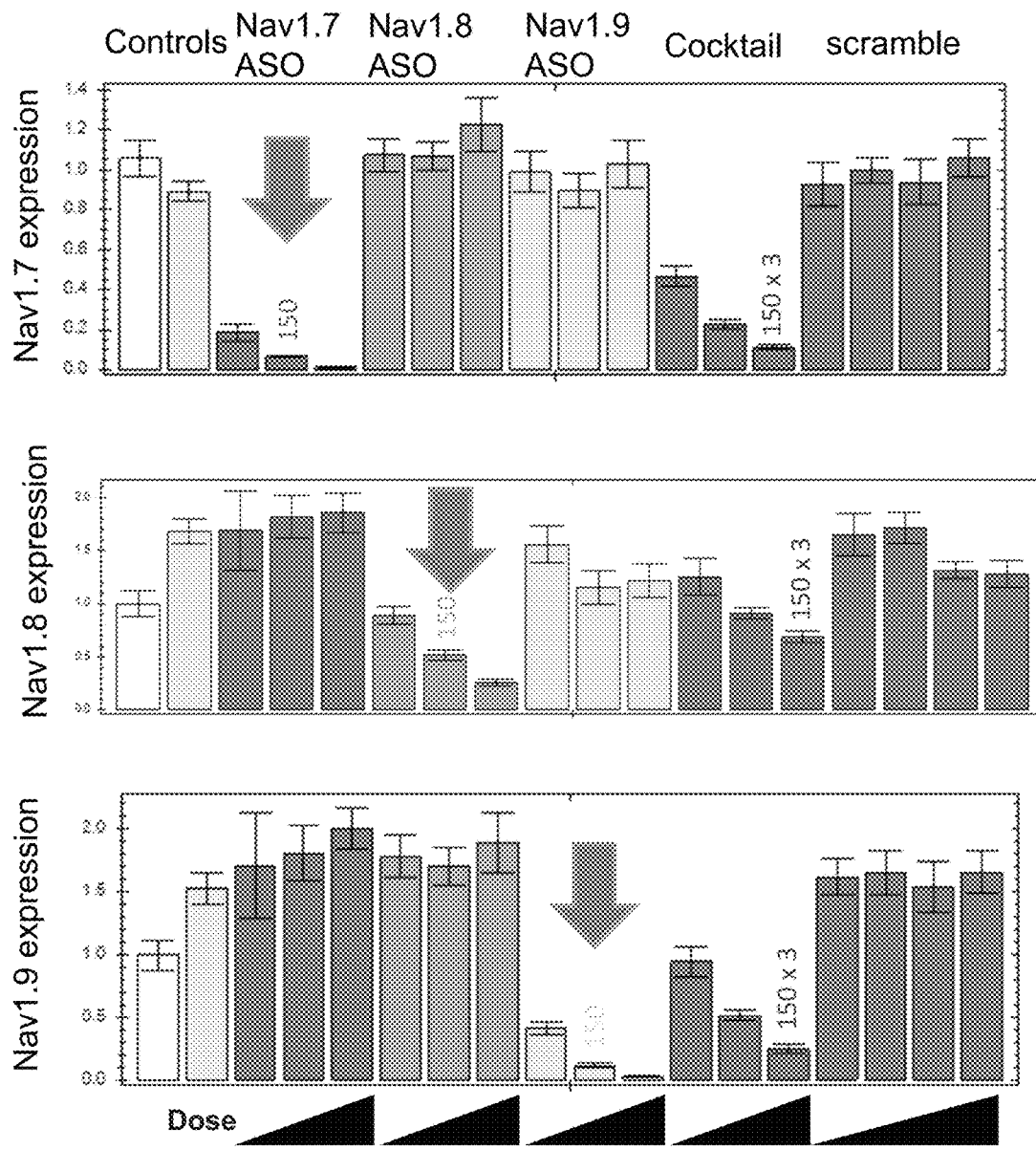
FIG. 7 shows the target selectivity of ASOs of the disclosure.

FIG. 7 shows the selectivity of rat NaV-targeted ASOs tested by qPCR in rat DRG. The top panel shows the effect on mRNA levels of delivery an ASO specific for NaV1.7. The middle panel shows the effect of delivering an ASO specific for NaV1.8; the bottom panel is for NaV1.9. In all panels, the fourth triad of bars gives the results for delivering a 450 nM cocktail ASO (150 nM NaV1.7 ASO+150 nM NaV1.8 ASO+150 nM NaV1.9 ASO). In each panel, the non-target NaV channel was not knocked down by the ASO (Nav1.7 ASO did not knock down expression of NaV1.8 or NaV 1.9, etc., showing target selectivity). The cocktail of 3 oligonucleotides 107 is shown to knock down all the three targets.

Figure 8:
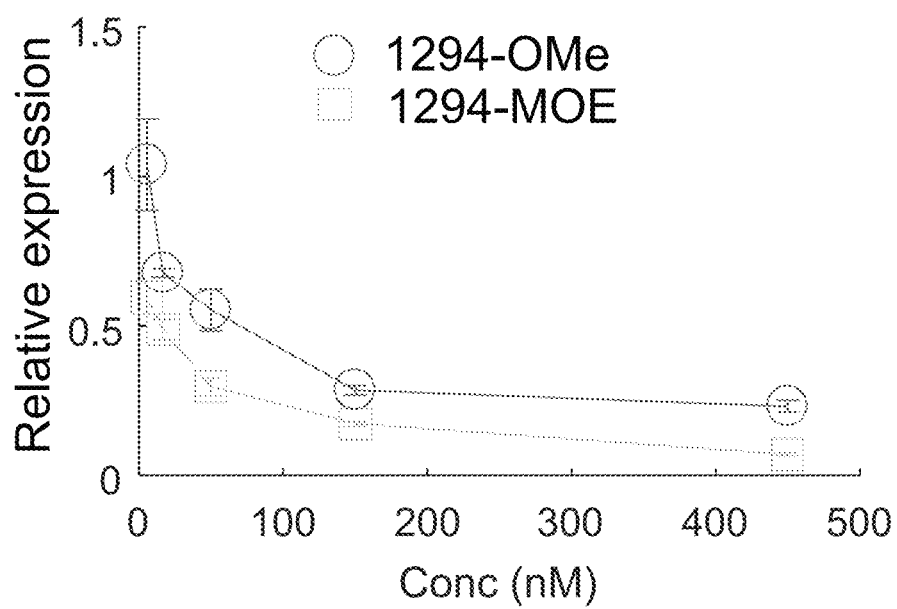
FIG. 8 compares the effects of ribose sugar modification on ASOs.

FIG. 8 compares the effects of ribose sugar modification within oligonucleotides 107 of the disclosure. An oligonucleotide 107 with a 20 base sequence matching the 20 bases beginning at position 1294 of the human SCN9A gene (SEQ ID NO: 6) was tested in a form with 2'-O-methyl-(OMe) and in a form with 2'-O-Methoxyethyl-(MOE) ribose sugar modifications. Similar tests were performed against the control oligo SEQ ID NO: 165. It was found that the oligonucleotide of the disclosure outperformed the control and also that, as shown, the MOE modification outperforms (shows a greater inhibition of target relative expression) the OMe modification. Thus it may be preferable for an oligonucleotide of the disclosure to include one or more 2'-O-methoxyethyl (MOE) modifications on RNA ribose sugars. For example, the ASOs may have 5' and 3' wings of about five RNA bases each, and in those wings most or all ribose sugars may be 2' MOE.

Nav1.7 and Nav1.8 ASO combination effects were tested in rat DRG neurons in vitro. The in vitro neurons included optogenetic constructs that provided neural activation under optical stimulus (e.g., a modified algal channelrhodopsin that causes the neuron to fire in response to light) and optical reporters of neural activity (modified archaerhodopsins that emit light in proportion to neuronal membrane voltage and yield signals of neuronal activity). The in vitro neurons were assayed in a fluorescence microscopy instrument, and were treated with a pain mediator composition (e.g., a simulated "cancer pain soup") that serves as an irritant causing DRG neurons to fire in a manner similar to the experience of pain in vivo. Any suitable optogenetic constructs, optogenetic microscope, or pain mediator compositions may be used.

For example, suitable optogenetic constructs include those described in U.S. Pat. No. 9,594,075, incorporated by reference. Suitable optogenetic microscopes include those described in U.S. Pat. No. 10,288,863, incorporated by reference. Suitable pain mediator compositions include those described in WO 2018/165577, incorporated by reference.

The in vitro DRG assays involve measuring light from an optogenetic neural sample alone, under increasing optical stimulation. This gives a baseline reading of neural excitability. Then, the neural sample is stimulated with an irritant, here, a pain mediator composition comprising a mixture of cytokines, proteases, pH, necrosis factors, or other factors that may be found in vivo at the site of a painful tumor. Light is measured from the neural sample under treatment with that irritant. Finally, the neural sample is treated with a composition of the disclosure. It is hypothesized that, where the irritant moves measured excitability away from the measured baseline, the oligonucleotides 107 will tend to restore measured excitability towards the baseline. It is further expected that NaV1.7 and NaV1.8 exhibit their effects under different (albeit overlapping) conditions of neural activity. The results show that anti-NaV1.7 and anti-NaV1.8 ASOs in combination mitigate neural response to painful irritants a greater amount and over a greater range of input stimulus levels relative to individual NaV 1.7 or NaV 1.8 ASOs.

Figure 9:
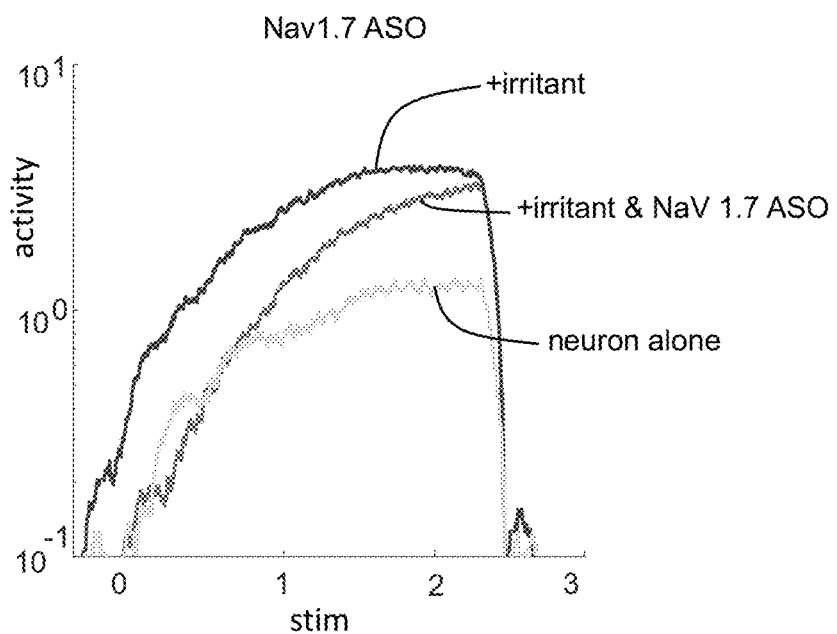
FIG. 9 shows effects of an anti-NaV1.7 ASO.

FIG. 9 shows a measured level of neural activity in response to an increasing ramp of blue light stimulation at a baseline, under treatment with the irritant, and under treatment with the irritant and an anti-NaV1.7 ASO. As expected, the NaV1.7 ASO decreases the neural excitability exhibited in response to the irritant.

Figure 10:
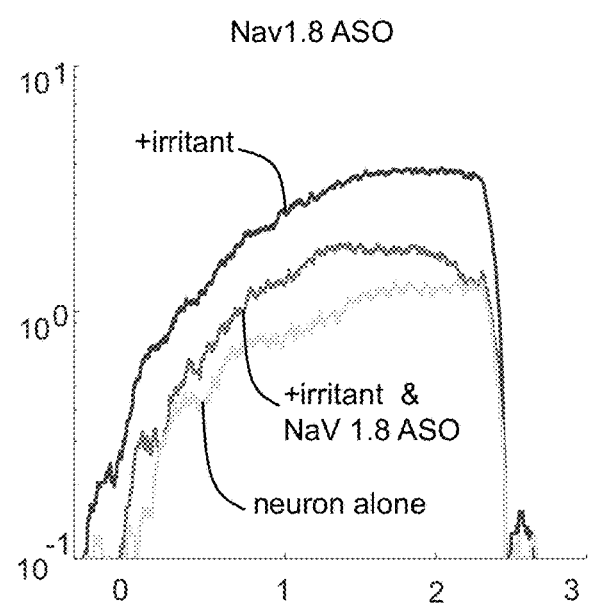
FIG. 10 shows effects of an anti-NaV1.8 ASO.

FIG. 10 shows a measured level of neural activity in response to an increasing ramp of blue light stimulation at a baseline, under treatment with the irritant, and under treatment with the irritant and an anti-NaV1.8 ASO. As expected, the NaV1.8 ASO decreases the neural excitability exhibited in response to the irritant, albeit in a different region of the input stimulus power.

Figure 11:
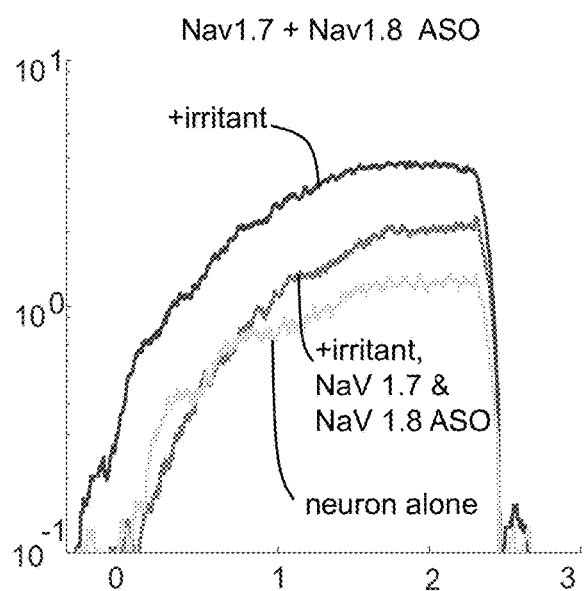
FIG. 11 shows neural activity levels under treatment with a combination composition.

FIG. 11 shows a measured level of neural activity in response to an increasing ramp of blue light stimulation at a baseline, under treatment with the irritant, and under treatment with the irritant and a composition comprising an anti-NaV1.7 ASO and an anti-NaV1.8 ASO. The net pain reducing effect of the combination of oligos is better than either oligo alone. The level of activity the DRG neurons is significantly lower across the full range of input stimulation. It may be found that a living subject experiencing a variety of painful conditions would benefit by a greater range and potency of analgesic effects by being administered a composition comprising different oligos that target different NaV channels.

Methods and compositions of the disclosure may beneficially be used for delivery of therapeutic oligonucleotides 107 described herein to dorsal root ganglion (DRG) neurons in vivo in a patient suffering pain. Any suitable delivery approach may be used including, for example, systemic delivery (e.g., by injection) or local delivery (e.g., by subcutaneous injections or implantation of a slow-release device). In some embodiments, a composition 101 of the disclosure is delivered by intrathecal injection. Methods of the disclosure may involve delivering a composition of the disclosure by intrathecal injection about every few months, e.g., about 3 or 4 times per year.

Intrathecal injection refers to a route of administration for drugs via an injection into the spinal canal, or into the subarachnoid space so that it reaches the cerebrospinal fluid (CSF) and is useful in spinal anesthesia, chemotherapy, or pain management applications. Intrathecal delivery avoids the composition from being stopped by the blood brain barrier. Preferably, the composition 101 is compounded in such a formulation so as not to contain any preservative or other potentially harmful inactive ingredients that are sometimes found in standard injectable drug preparations. The composition 101 may be provided in an intrathecal pump, or it may be provided in a formulation suitable for reconstitution in the clinic for delivery via an intrathecal pump. For example, the composition 101 may be in solution (e.g., in saline) at a defined concentration. A technician can mix the concentration with a suitable diluent at the clinic for delivery. In other embodiments, the ASOs are lyophilized or otherwise preserved in a dry, solid form, to be resuspended and appropriately diluted in the clinic. Intrathecal delivery reduces concerns about PK, metabolism, peripheral on/off target effects. Intrathecal administration approaches have been validated for clinical use with other drugs such as Ziconotide and ASOs such as nusinersen. Such methods may be used to deliver compositions 101 of the disclosure directly to the nervous system.

An oligonucleotide of the disclosure, such as a gapmer, ASO, or therapeutic oligonucleotide 107 in a composition 101 may have a sequence defined with reference to one of the sequences set forth in Table 1. For example, an oligonucleotide of the disclosure may have a sequence that is at least about 75%, 80%, 90%, 95%, or perfectly identical to one of SEQ ID NO. 1-141 as set forth in Table 1. The top preferred embodiments against SCN9A include those in Table 1 labeled as follows: "4/6" (SEQ ID NO: 6); "4/10" (SEQ ID NO: 10); and "4/11" (SEQ ID NO: 11). Those three candidates show robust and significant knockdown activity (>75%) of NaV 1.7 in a dose-dependent manner. The top preferred embodiments against SCN10A include those in Table 1 labeled as: "5/8" (SEQ ID NO: 61); "5/18" (SEQ ID NO: 71); "5/20" (SEQ ID NO: 73). Those three candidates show robust and significant knockdown activity (>65%) of NaV 1.8 in a dose-dependent manner. The top preferred embodiments against SCN11A include those in Table 1 labeled: "6/1" (SEQ ID NO: 102); "6/3" (SEQ ID NO: 104); and "6/6" (SEQ ID NO: 107). Those three candidates show robust and significant knockdown activity (>70%) of NaV 1.9 in a dose-dependent manner.

TABLE 1

Sequences for therapeutic oligonucleotide

| Ref. No. (Target code/No.) | Sequence | SEQ ID NO | Target ((i) for intronic) |
|---|---|---|---|
| 4/1 | GCCAGTTCCACGGGTCACGA | (SEQ ID NO: 1) | SCN9A |
| 4/2 | ATCCAGCCAGTTCCACGGGT | (SEQ ID NO: 2) | SCN9A |
| 4/3 | CAGGTGTACCCCTCTGGACA | (SEQ ID NO: 3) | SCN9A |
| 4/4 | AGCACGCAGCGTCTGTTGGT | (SEQ ID NO: 4) | SCN9A |
| 4/5 | TGCCAGCAGCACGCAGCGTC | (SEQ ID NO: 5) | SCN9A |
| 4/6 | TTGCCAGCAGCACGCAGCGT | (SEQ ID NO: 6) | SCN9A |
| 4/7 | TTTGCCAGCAGCACGCAGCG | (SEQ ID NO: 7) | SCN9A |
| 4/8 | GTTTTGCCAGCAGCACGCAG | (SEQ ID NO: 8) | SCN9A |
| 4/9 | GTTTGCCTGGTTCTGTTCTT | (SEQ ID NO: 9) | SCN9A |
| 4/10 | TGTGCTCGCCTATGCCCTTC | (SEQ ID NO: 10) | SCN9A |
| 4/11 | GTTCTGCTGCTTCGCCTTGC | (SEQ ID NO: 11) | SCN9A |
| 4/12 | CCCCTTCTGCTCTCATTGTC | (SEQ ID NO: 12) | SCN9A |
| 4/13 | GCCCTTCTGCTCTCATTGT | (SEQ ID NO: 13) | SCN9A |
| 4/14 | GAGCCCCTTCTGCTCTCATT | (SEQ ID NO: 14) | SCN9A |
| 4/15 | GTGAGCCCCTTCTGCTCTCA | (SEQ ID NO: 15) | SCN9A |
| 4/16 | AGTGAGCCCCTTCTGCTCTC | (SEQ ID NO: 16) | SCN9A |
| 4/17 | ACTGCTGCGTCGCTCCTGGG | (SEQ ID NO: 17) | SCN9A |
| 4/18 | GCATTTTCCCGTTCACCGGC | (SEQ ID NO: 18) | SCN9A |
| 4/19 | TGCAGTCCACAGCACTGTGC | (SEQ ID NO: 19) | SCN9A |
| 4/20 | GCATGAGGGCTGAGCGTCCA | (SEQ ID NO: 20) | SCN9A |
| 4/21 | CTCTCAGGGCTGCTTCTTTT | (SEQ ID NO: 21) | SCN9A |
| 4/22 | CTGTTTGCCAGCTTCCAAGT | (SEQ ID NO: 22) | SCN9A |
| 4/23 | TTGGTCCAGTCCGGTGGGTT | (SEQ ID NO: 23) | SCN9A |

TABLE 1-continued

Sequences for therapeutic oligonucleotide

| Ref. No. (Target code/No.) | Sequence | SEQ ID NO | Target ((i) for intronic) |
|---|---|---|---|
| 4/27 | TTGCCTCAGCTTCTTCTTGC | (SEQ ID NO: 24) | SCN9A |
| 4/31 | GTTGCAGTCCACAGCACTGT | (SEQ ID NO: 25) | SCN9A |
| 4/33 | AGGTTACCTAGAGCCCCTAC | (SEQ ID NO: 26) | SCN9A |
| 4/34 | GGTTGTTTGCATCAGGGTCT | (SEQ ID NO: 27) | SCN9A |
| 4/35 | AGGTTCAGCCTCTGCTTCTT | (SEQ ID NO: 28) | SCN9A |
| 4/36 | CTTGGACCCCAGCTTTTTCA | (SEQ ID NO: 29) | SCN9A |
| 4/37 | GGGTTACCACAGTCTCCTTC | (SEQ ID NO: 30) | SCN9A |
| 4/38 | GAATCCATCTCCCCACTCTC | (SEQ ID NO: 31) | SCN9A |
| 4/39 | GCTGCCCACCTTTCTTAGGA | (SEQ ID NO: 32) | SCN9A |
| 4/40 | GCCAATTCCCTGGCCATCCT | (SEQ ID NO: 33) | SCN9A |
| 4/41 | CCTTGGGATCTCTGCCAGGT | (SEQ ID NO: 34) | SCN9A (i) |
| 4/42 | GTCCCTGGAGTCTTGTCTGA | (SEQ ID NO: 35) | SCN9A (i) |
| 4/43 | CTCCCATATCTCCAGTCTGC | (SEQ ID NO: 36) | SCN9A (i) |
| 4/44 | GCTCTTGCTCTGGTTCAGCT | (SEQ ID NO: 37) | SCN9A (i) |
| 4/45 | GGTTCTTCCAGCTTCTCTGC | (SEQ ID NO: 38) | SCN9A (i) |
| 4/46 | CATGTCCCTGTCCATCCCTA | (SEQ ID NO: 39) | SCN9A (i) |
| 4/47 | GTGTGGCAGCAGTGACCAGT | (SEQ ID NO: 40) | SCN9A (i) |
| 4/48 | CCCTTGTGCTGGGTCTATGT | (SEQ ID NO: 41) | SCN9A (i) |
| 4/49 | GCTCTACCCTAGCTGTCAGG | (SEQ ID NO: 42) | SCN9A (i) |
| 4/50 | GCTCCTCCTCAGAGTTTTGC | (SEQ ID NO: 43) | SCN9A (i) |
| 4/51 | GAGCCTCTTCTCTTCAGGCC | (SEQ ID NO: 44) | SCN9A (i) |
| 4/52 | TGGCTCATCCAGGCTCATCA | (SEQ ID NO: 45) | SCN9A (i) |
| 4/53 | GCATTATTCCCACCAGGTCC | (SEQ ID NO: 46) | SCN9A (i) |
| 4/54 | TCTCTTCAGTCTCCTCCACA | (SEQ ID NO: 47) | SCN9A (i) |
| 4/55 | CCAGCAGTTGGCAGAGGTTC | (SEQ ID NO: 48) | SCN9A (i) |
| 4/56 | GCTTGTGCATCCCAGTGCCT | (SEQ ID NO: 49) | SCN9A (i) |
| 4/57 | CCTCCATCTGATTCCTCCTC | (SEQ ID NO: 50) | SCN9A (i) |
| 4/58 | GCCTTCTCACCAGTGCTGCT | (SEQ ID NO: 51) | SCN9A (i) |
| 4/59 | TCTAGCCTTCTCACCAGTGC | (SEQ ID NO: 52) | SCN9A (i) |
| 4/60 | GGTGGCAGGTCAAGCAGGGT | (SEQ ID NO: 53) | SCN9A (i) |
| 5/1 | TCTTGGTCCTTCTGCTCCCT | (SEQ ID NO: 54) | SCN10A |
| 5/2 | GCTCCCCGATCAGTTCTGCT | (SEQ ID NO: 55) | SCN10A |
| 5/3 | TGTCCGGTGTGTGCTGTAGA | (SEQ ID NO: 56) | SCN10A |
| 5/4 | TGGTCCTCCCTTTGTTCAGC | (SEQ ID NO: 57) | SCN10A |
| 5/5 | GTTGCAGCCCCACCAAGGCA | (SEQ ID NO: 58) | SCN10A |
| 5/6 | GGGTCTGCTGGTAGAGGCGT | (SEQ ID NO: 59) | SCN10A |
| 5/7 | GCACCTCCTGCTCCTTCCGG | (SEQ ID NO: 60) | SCN10A |

TABLE 1-continued

Sequences for therapeutic oligonucleotide

| Ref. No. (Target code/No.) | Sequence | SEQ ID NO | Target ((i) for intronic) |
|---|---|---|---|
| 5/8 | GTTGTCTTCTGTGGAGCCCT | (SEQ ID NO: 61) | SCN10A |
| 5/9 | GCTGGTCAAGCAGGGTGGGC | (SEQ ID NO: 62) | SCN10A |
| 5/10 | GGCCACGCCCAGCTCTAGCA | (SEQ ID NO: 63) | SCN10A |
| 5/11 | GGTGAGGTTCCCCAGTGCCC | (SEQ ID NO: 64) | SCN10A |
| 5/12 | GTCGTGCATGTGCCAGCGGG | (SEQ ID NO: 65) | SCN10A |
| 5/13 | TCCGTGCCAGGGCCACCTGC | (SEQ ID NO: 66) | SCN10A |
| 5/14 | GGGAGCTTGGAGCCCTCCAG | (SEQ ID NO: 67) | SCN10A |
| 5/15 | GTTCCAGTGCCTGGGCTCCT | (SEQ ID NO: 68) | SCN10A |
| 5/16 | CCAGCTCAGGGATCTTCCTC | (SEQ ID NO: 69) | SCN10A |
| 5/17 | GTCTTGCGCACCTGCCAGCC | (SEQ ID NO: 70) | SCN10A |
| 5/18 | CGTGGGCTTCTGGTCCAGGT | (SEQ ID NO: 71) | SCN10A |
| 5/19 | GCCCGCAGTGGCCGCAGAGC | (SEQ ID NO: 72) | SCN10A |
| 5/20 | GGGCATCCACCACCACCCGC | (SEQ ID NO: 73) | SCN10A |
| 5/21 | GGCGCCCACCAGGGCATCCA | (SEQ ID NO: 74) | SCN10A |
| 5/22 | TGTCCTCCCACTTGGGTTGC | (SEQ ID NO: 75) | SCN10A |
| 5/23 | TCCCCTCTGGTGCCATTGCT | (SEQ ID NO: 76) | SCN10A |
| 5/24 | GGGCTCCCACAGTCCCCTCT | (SEQ ID NO: 77) | SCN10A |
| 5/25 | GCAGCCTCCTCCTCAGCTCT | (SEQ ID NO: 78) | SCN10A |
| 5/26 | GCCATATCCTCACCCTCTCA | (SEQ ID NO: 79) | SCN10A (i) |
| 5/27 | GGGACTGCTTTCTCCCTTCC | (SEQ ID NO: 80) | SCN10A (i) |
| 5/28 | TGCCTTGTCTCTGGCCTCCC | (SEQ ID NO: 81) | SCN10A (i) |
| 5/29 | GCTTGTTTCCAGTCCTCAGC | (SEQ ID NO: 82) | SCN10A (i) |
| 5/30 | GACCTTCCTCCCACAGTGCC | (SEQ ID NO: 83) | SCN10A (i) |
| 5/31 | GAGCCACCCTCCCACACAGC | (SEQ ID NO: 84) | SCN10A (i) |
| 5/32 | ACAGCAGTGTCTCCTTGGCC | (SEQ ID NO: 85) | SCN10A (i) |
| 5/33 | CCCAGTGTCCACATGTCTCC | (SEQ ID NO: 86) | SCN10A (i) |
| 5/34 | TCTGTTGCTCCCACCAGCTT | (SEQ ID NO: 87) | SCN10A (i) |
| 5/35 | GCCTCTTCTGTGGAGGTGGG | (SEQ ID NO: 88) | SCN10A (i) |
| 5/36 | CCACTCACCACCAGGTTCCC | (SEQ ID NO: 89) | SCN10A (i) |
| 5/37 | GGTCTCCTCTGCATTTCCCT | (SEQ ID NO: 90) | SCN10A (i) |
| 5/38 | GCCCTGCATGTTCCTGAGGC | (SEQ ID NO: 91) | SCN10A (i) |
| 5/39 | GCTGGCTGTCCAACCTCTCC | (SEQ ID NO: 92) | SCN10A (i) |
| 5/40 | CCAGCCTCTACCAGCCCACT | (SEQ ID NO: 93) | SCN10A (i) |
| 5/41 | GCCCTCCCTCTTATCTTACC | (SEQ ID NO: 94) | SCN10A (i) |
| 5/42 | GCCACCCTAGTTTTCCTCCC | (SEQ ID NO: 95) | SCN10A (i) |
| 5/43 | GGTGCCAGCCTGTTCAGTCC | (SEQ ID NO: 96) | SCN10A (i) |
| 5/44 | GTCCACCCAAGCCCACCTCC | (SEQ ID NO: 97) | SCN10A (i) |

TABLE 1-continued

Sequences for therapeutic oligonucleotide

| Ref. No. (Target code/No.) | Sequence | SEQ ID NO | Target ((i) for intronic) |
|---|---|---|---|
| 5/45 | GGAACTCCCTGCCCAGCCTC | (SEQ ID NO: 98) | SCN10A (i) |
| 5/46 | GTCTGGGTCCTGGTGGCTGT | (SEQ ID NO: 99) | SCN10A (i) |
| 5/47 | GCCCTGCCAGTCACACTGCC | (SEQ ID NO: 100) | SCN10A (i) |
| 5/48 | GGCTGATCCTTGCCTTCTGC | (SEQ ID NO: 101) | SCN10A (i) |
| 6/1 | TTGCTCTAGGAGCTGTGGCT | (SEQ ID NO: 102) | SCN11A |
| 6/2 | AGCACTCAGTGCTCTCTGCC | (SEQ ID NO: 103) | SCN11A |
| 6/3 | GATGGTGATGGCCAGCTCAG | (SEQ ID NO: 104) | SCN11A |
| 6/4 | GGCCTCCATCTTGTGATGCT | (SEQ ID NO: 105) | SCN11A |
| 6/5 | AGGGCTCCGACAGAGTTGCC | (SEQ ID NO: 106) | SCN11A |
| 6/6 | GTCAGGCTTCCAAGGGCTCC | (SEQ ID NO: 107) | SCN11A |
| 6/7 | AGTCAGGCTTCCAAGGGCTC | (SEQ ID NO: 108) | SCN11A |
| 6/8 | GGACCACAGTCAGGCTTCCA | (SEQ ID NO: 109) | SCN11A |
| 6/9 | GTCGGGCCTGTCGGGTTACA | (SEQ ID NO: 110) | SCN11A |
| 6/10 | TGTCGGGCCTGTCGGGTTAC | (SEQ ID NO: 111) | SCN11A |
| 6/11 | CTGTCGGGCCTGTCGGGTTA | (SEQ ID NO: 112) | SCN11A |
| 6/12 | ACTGTCGGGCCTGTCGGGTT | (SEQ ID NO: 113) | SCN11A |
| 6/13 | GACTGTCGGGCCTGTCGGGT | (SEQ ID NO: 114) | SCN11A |
| 6/14 | AGACTGTCGGGCCTGTCGGG | (SEQ ID NO: 115) | SCN11A |
| 6/15 | CCCCATGTGCCAGTGCCGTA | (SEQ ID NO: 116) | SCN11A |
| 6/16 | CCTGGGTCTCTGAGCCCCTT | (SEQ ID NO: 117) | SCN11A |
| 6/17 | TCCTGGGTCTCTGAGCCCCT | (SEQ ID NO: 118) | SCN11A |
| 6/18 | AAGCTCCTCCTGGGTCTCTG | (SEQ ID NO: 119) | SCN11A |
| 6/19 | GTGGGCTTCTTGTTCTCCTG | (SEQ ID NO: 120) | SCN11A |
| 6/20 | GTAGCAGGTTTTCCGCAGGT | (SEQ ID NO: 121) | SCN11A |
| 6/21 | GGTACTAGCTCCTCCTGCCT | (SEQ ID NO: 122) | SCN11A (i) |
| 6/22 | CATCCACCTCCAGACCTCCC | (SEQ ID NO: 123) | SCN11A (i) |
| 6/23 | GCCCAAGTCCCTCAAGCCTT | (SEQ ID NO: 124) | SCN11A (i) |
| 6/24 | GGTTCCAGGTTCCACCCAGC | (SEQ ID NO: 125) | SCN11A (i) |
| 6/25 | CTGTCTCCTCCATAGGTCCT | (SEQ ID NO: 126) | SCN11A (i) |
| 6/26 | TTCCTCCCTGCCTTATGGGT | (SEQ ID NO: 127) | SCN11A (i) |
| 6/27 | GCTCCTCCTTGCTTCAGGCT | (SEQ ID NO: 128) | SCN11A (i) |
| 6/28 | GCATCCAGGCATCTCAGTGC | (SEQ ID NO: 129) | SCN11A (i) |
| 6/29 | GCCCTATGCCTGCCTCAGTG | (SEQ ID NO: 130) | SCN11A (i) |
| 6/30 | CCACACCTGTCTGCCTGTGT | (SEQ ID NO: 131) | SCN11A (i) |
| 6/31 | GTGTCCTCTGCCTCTCTACT | (SEQ ID NO: 132) | SCN11A (i) |
| 6/32 | CCTGCCTTCTCAGAGTGCCA | (SEQ ID NO: 133) | SCN11A (i) |
| 6/33 | GCCCTCTTTCTCACCAGACC | (SEQ ID NO: 134) | SCN11A (i) |

TABLE 1-continued

Sequences for therapeutic oligonucleotide

| Ref. No. (Target code/No.) | Sequence | SEQ ID NO | Target ((i) for intronic) |
|---|---|---|---|
| 6/34 | CCCATGTCCCTACCTCCTTT | (SEQ ID NO: 135) | SCN11A (i) |
| 6/35 | GTCCCATCCCAAGTCTAGCC | (SEQ ID NO: 136) | SCN11A (i) |
| 6/36 | TCTTTAGGTCCTGTTGCCCT | (SEQ ID NO: 137) | SCN11A (i) |
| 6/37 | CCCACTCCTCCCTTCTTTGA | (SEQ ID NO: 138) | SCN11A (i) |
| 6/38 | GGGCTCTCTTCACTCTGCCT | (SEQ ID NO: 139) | SCN11A (i) |
| 6/39 | GGGTCCTCTCTGTTGCCACT | (SEQ ID NO: 140) | SCN11A (i) |
| 6/40 | CTCCCTAGCCCTGCCTCTTC | (SEQ ID NO: 141) | SCN11A (i) |
| 4/61 | AAAATCCAGCCAGTTCCAC | (SEQ ID NO: 142) | SCN9A/SCN10A |
| 4/62 | CAAAATCCAGCCAGTTCCA | (SEQ ID NO: 143) | SCN9A/SCN10A |
| 4/63 | TGCAATGTACATGTTCACC | (SEQ ID NO: 144) | SCN9A/SCN10A |
| 4/64 | CTGCAATGTACATGTTCAC | (SEQ ID NO: 145) | SCN9A/SCN10A |
| 4/65 | ACTGCAATGTACATGTTCA | (SEQ ID NO: 146) | SCN9A/SCN10A |
| 4/66 | TGACTGCAATGTACATGTT | (SEQ ID NO: 147) | SCN9A/SCN10A |
| 4/67 | ATGACTGCAATGTACATGT | (SEQ ID NO: 148) | SCN9A/SCN10A |
| 4/68 | GTCATTTTTGCCATGTTAT | (SEQ ID NO: 149) | SCN9A/SCN10A |
| 4/69 | TCAAATAACCCAGAAGCCT | (SEQ ID NO: 150) | SCN9A/SCN10A |
| 4/70 | TTCAAATAACCCAGAAGCC | (SEQ ID NO: 151) | SCN9A/SCN10A |
| 4/71 | TTTCAAATAACCCAGAAGC | (SEQ ID NO: 152) | SCN9A/SCN10A |
| 5/49 | AAAATCCAGCCAGTTCCAA | (SEQ ID NO: 153) | SCN9A/SCN10A |
| 5/50 | AGGCCTGGGATCACAGAAA | (SEQ ID NO: 154) | SCN9A/SCN10A |
| 5/51 | CAGGCCTGGGATCACAGAA | (SEQ ID NO: 155) | SCN9A/SCN10A |
| 5/52 | TCAGGCCTGGGATCACAGA | (SEQ ID NO: 156) | SCN9A/SCN10A |
| 5/53 | TTCAGGCCTGGGATCACAG | (SEQ ID NO: 157) | SCN9A/SCN10A |
| 5/54 | CTTCAGGCCTGGGATCACA | (SEQ ID NO: 158) | SCN9A/SCN10A |
| 5/55 | TGCTCTGTGAATAAATGCT | (SEQ ID NO: 159) | SCN9A/SCN10A |
| 5/56 | TAATTTGGCATCTGTCTTT | (SEQ ID NO: 160) | SCN9A/SCN10A |
| 5/57 | TCAGATAACCCAGAAGCCT | (SEQ ID NO: 161) | SCN9A/SCN10A |
| 5/58 | TTCAGATAACCCAGAAGCC | (SEQ ID NO: 162) | SCN9A/SCN10A |
| 5/59 | TTTCAGATAACCCAGAAGC | (SEQ ID NO: 163) | SCN9A/SCN10A |
| 5/60 | GGATGATGAATAGATGGAA | (SEQ ID NO: 164) | SCN9A/SCN10A |
| C/1 | GCCAUAAUCCGGGUUCUGC | (SEQ ID NO: 165) | ctrl |

As discussed above, a measured level of neural activity at a baseline, under treatment with an irritant, and under treatment with the irritant and a composition comprising an anti-NaV1.7 ASO and an anti-NaV1.8 ASO show that the combination of oligos performs better than either oligo alone. As disclosed herein, the top preferred embodiments against SCN9A (aka NaV1.7) include those with one of SEQ ID NO: 6; SEQ ID NO: 10; or SEQ ID NO: 11. The top preferred embodiments against SCN10A (aka NaV1.9) include those with one of SEQ ID NO: 61; SEQ ID NO: 71; or SEQ ID NO: 73. Accordingly, a most preferred combination embodiment of the disclosure includes a composition for treating pain. The composition includes: a first oligonucleotide that hybridizes to an mRNA encoding a sodium channel protein along a segment of the mRNA that is at least about 90% complementary to one of SEQ ID NO: 6; SEQ ID NO: 10; and SEQ ID NO: 11; and a second oligonucleotide that hybridizes to an mRNA encoding a sodium channel protein along a segment of the mRNA that is at least about 90% complementary to one of SEQ ID NO: 61; SEQ ID NO: 71; and SEQ ID NO: 73. In the preferred combination embodiments, each of the therapeutic oligonucleotides may have a gapmer structure that includes a central DNA segment flanked by modified RNA wings.

Either or both of the wings may include modified RNA bases, e.g., both wings may include 5 consecutive RNA bases with 2'-O-methoxyethyl ribose modifications. The entirety of each oligonucleotide may be connected via phosphodiester or phosphorothioate linkages or others as will be apparent to the skilled artisan. Preferably the plurality of therapeutic oligonucleotides is provided lyophilized or in solution, for dilution or reconstitution in a clinic for intrathecal injection. That is, packaged in one or more tubes, lyophilized or in solution, are at least thousand to millions of copies of the first oligonucleotide and at least thousand to millions of copies of the second oligonucleotide. Exhibiting the effects as demonstrated by FIG. 11, this preferred combination embodiment of the composition may prove to have unexpected benefits as a non-opioid therapeutic for the treatment of pain.

Other features and embodiments are within the scope of the disclosure. Embodiments of the disclosure include oligonucleotides, including locked nucleic acid (LNA) antisense oligonucleotides targeting SCN9A or SCN10A which are capable of inhibiting the expression of NaV1.7 or NaV 1.8 in a cell which is expressing NaV1.7 and/or NaV1.8. The oligonucleotide of the invention may be used in the prevention or treatment of pain. The invention further provides advantageous target site sequences on the human NaV1.7 pre-mRNA which may be targeted by oligonucleotide inhibitors of human NaV1.7 such as antisense oligonucleotides or RNAi agents, such as siRNAs or shRNAs.

The invention provides for an oligonucleotide of 10 to 30 nucleotides in length, which comprises a contiguous nucleotide sequence of 10 to 30 nucleotides in length with at least 90% complementarity, such as 100% complementarity, to a human NaV1.7 target nucleic acid and a human NaV1.8 target nucleic acid, and which is capable of inhibiting the expression of both NaV1.7 or NaV1.8 in a cell. An oligonucleotide 107 may be 100% identical to one of SEQ ID NO 1-141, or is at least 90% identical.

Embodiments include a pharmaceutically acceptable salt of the antisense oligonucleotide according to the invention, or the conjugate according to the invention.

The invention provides a pharmaceutical composition comprising the antisense oligonucleotide of the invention or the conjugate of the invention and a pharmaceutically acceptable diluent, solvent, carrier, salt and/or adjuvant.

The invention provides for the antisense oligonucleotide of the invention or the conjugate of the invention or the pharmaceutical salt or composition of the invention for use in medicine.

The invention provides for the antisense oligonucleotide of the invention or the conjugate of the invention or the pharmaceutical salt or composition of the invention for use in the treatment or prevention or alleviation of pain. The invention provides for the use of the antisense oligonucleotide of the invention or the conjugate of the invention or the pharmaceutical salt or composition of the invention, for the preparation of a medicament for the treatment, prevention or alleviation of pain.

In some embodiments the pain is chronic pain, neuropathic pain, inflammatory pain, spontaneous pain, or nociceptive pain.

Oligonucleotides are commonly made in the laboratory by solid-phase chemical synthesis followed by purification and isolation. When referring to a sequence of the oligonucleotide, reference is made to the sequence or order of nucleobase moieties, or modifications thereof, of the covalently linked nucleotides or nucleosides. The oligonucleotide of the invention may be man-made, i.e., chemically synthesized, and is typically purified or isolated. The oligonucleotide of the invention may comprise one or more modified nucleosides or nucleotides, such as 2' sugar modified nucleosides.

The modified nucleotides may be independently selected from the group consisting of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxl-modified nucleotide, a 2'-methoxyethyl modified nucleotide, a 2'-O-alkyl-modified nucleotide, a morpholino nucleotide, a phosphoramidate, a non-natural base comprising nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, a nucleotide comprising a 5'-phosphate mimic, a glycol modified nucleotide, and a 2'-O—(N-methylacetamide) modified nucleotide, and combinations thereof.

The nitrogenous bases of the ASO may be naturally occurring nucleobases such as adenine, guanine, cytosine, thymidine, uracil, xanthine and hypoxanthine, as well as non-naturally occurring variants, such as substituted purine or substituted pyrimidine, such as nucleobases selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

An oligonucleotide 107 of the disclosure is capable of down-regulating (inhibiting) the expression of a sodium channel (NaV1.7, 1.8, or 1.9). In some embodiments the antisense oligonucleotide of the invention is capable of modulating the expression of the target by inhibiting or down-regulating it. Preferably, such modulation produces an inhibition of expression of at least 20% compared to the normal expression level of the target, more preferably at least 30%, at least 40%, at least 50%, at least 60%, at least 70%, at least 80%, or at least 90% inhibition compared to the normal expression level of the target.

An antisense oligonucleotide (ASO) of the disclosure may decrease the level of the target nucleic acid (e.g. via RNase H cleavage), or may decrease the functionality (or alter the functionality) of the target nucleic acid, e.g. via modulation of splicing of a pre-mRNA.

An oligonucleotide 107 of the disclosure may comprise one or more nucleosides which have a modified sugar moiety, i.e. a modification of the sugar moiety when compared to the ribose sugar moiety found in DNA and RNA. Numerous nucleosides with modification of the ribose sugar moiety have been made, primarily with the aim of improving certain properties of oligonucleotides, such as affinity and/or nuclease resistance. Such modifications include those where the ribose ring structure is modified, e.g. by replacement with a hexose ring (HNA), or a bicyclic ring, which typically have a bridge between the C2 and C4 carbons on the ribose ring (LNA), or an unlinked ribose ring which typically lacks a bond between the C2 and C3 carbons (e.g. UNA). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions.

The oligonucleotide may include one or more Locked Nucleic Acid (LNA) bases. An LNA may include a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex. Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, and WO 2008/150729, all incorporated by reference.

Pharmaceutically acceptable salts of oligonucleotides of the disclosure include those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, a sulfonic acid, or salicylic acid. In addition, those salts may be prepared from addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins.

An oligonucleotide 107 may mediate or promote nuclease mediated degradation of sodium channel pre-mRNA or mRNA transcripts. Nuclease mediated degradation refers to an oligonucleotide capable of mediating degradation of a complementary nucleotide sequence when forming a duplex with such a sequence. In some embodiments, the oligonucleotide may function via nuclease mediated degradation of the target nucleic acid, where the oligonucleotides of the invention are capable of recruiting a nuclease, particularly an endonuclease, preferably endoribonuclease (RNase), such as RNase H. Examples of oligonucleotide designs which operate via nuclease mediated mechanisms are oligonucleotides which typically comprise a region of at least 5 or 6 consecutive DNA nucleosides and are flanked on one side or both sides by affinity enhancing nucleosides, for example gapmers. The RNase H activity of an antisense oligonucleotide 107 refers to its ability to recruit RNase H when in a duplex with a complementary RNA molecule.

The antisense oligonucleotide 107 of the invention, or contiguous nucleotide sequence thereof, may be a gapmer, also termed gapmer oligonucleotide or gapmer designs. The antisense gapmers are commonly used to inhibit a target nucleic acid via RNase H mediated degradation. A gapmer oligonucleotide comprises at least three distinct structural regions a 5'-flank, a gap and a 3'-flank, F-G-F' in the '5->3' orientation. The "gap" region (G) comprises a stretch of contiguous DNA nucleotides which enable the oligonucleotide to recruit RNase H. The gap region is flanked by a 5' flanking region (F) comprising one or more sugar modified nucleosides, advantageously high affinity sugar modified nucleosides, and by a 3' flanking region (F') comprising one or more sugar modified nucleosides, advantageously high affinity sugar modified nucleosides. The one or more sugar modified nucleosides in region F and F' enhance the affinity of the oligonucleotide for the target nucleic acid (i.e. are affinity enhancing sugar modified nucleosides). In some embodiments, the one or more sugar modified nucleosides in region F and F' are 2' sugar modified nucleosides, such as high affinity 2' sugar modifications, such as independently selected from LNA and 2'-MOE.

A mixed wing gapmer is an LNA gapmer wherein one or both of region F and F' comprise a 2' substituted nucleoside, such as a 2' substituted nucleoside independently selected from the group consisting of 2'-O-alkyl-RNA units, 2'-O-methyl-RNA, 2'-amino-DNA units, 2'-fluoro-DNA units, 2'-alkoxy-RNA, MOE units, arabino nucleic acid (ANA) units, 2'-fluoro-ANA units, or combinations thereof. In some embodiments wherein at least one of region F and F', or both region F and F' comprise at least one LNA nucleoside, the remaining nucleosides of region F and F' are independently selected from the group consisting of 2'-MOE and LNA. In some embodiments wherein at least one of region F and F', or both region F and F' comprise at least two LNA nucleosides, the remaining nucleosides of region F and F' are independently selected from the group consisting of 2'-MOE and LNA. In some mixed wing embodiments, one or both of region F and F' may further comprise one or more DNA nucleosides. Gapmer designs are discussed in WO 2008/049085 and WO 2012/109395, both incorporated by reference.

Conjugation of the oligonucleotide 107 to one or more non-nucleotide moieties may improve the pharmacology of the oligonucleotide, e.g. by affecting the activity, cellular distribution, cellular uptake or stability of the oligonucleotide. In some embodiments the conjugate moiety can modify or enhance the pharmacokinetic properties of the oligonucleotide by improving cellular distribution, bioavailability, metabolism, excretion, permeability, and/or cellular uptake of the oligonucleotide. In particular, the conjugate may target the oligonucleotide to a specific organ, tissue or cell type and thereby enhance the effectiveness of the oligonucleotide in that organ, tissue or cell type. The conjugate may also serve to reduce activity of the oligonucleotide in non-target cell types, tissues or organs, e.g. off target activity or activity in non-target cell types, tissues or organs.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof.

Oligonucleotides 107 of the disclosure may be provided in pharmaceutical compositions that include any of the aforementioned oligonucleotides and/or oligonucleotide conjugates or salts thereof and a pharmaceutically acceptable diluent, carrier, salt and/or adjuvant. A pharmaceutically acceptable diluent includes ACSF artificial cerebrospinal fluid and pharmaceutically acceptable salts include, but are not limited to, sodium and potassium salts. In some embodiments the pharmaceutically acceptable diluent is sterile phosphate buffered saline or sterile sodium carbonate buffer. In some preferred embodiments, diluents for clinical application include Elliott's B solution and/or ACSF artificial cerebrospinal fluid.

In some embodiments the oligonucleotide of the invention is in the form of a solution in the pharmaceutically acceptable diluent, for example dissolved in PBS or sodium carbonate buffer. The oligonucleotide may be pre-formulated in the solution or in some embodiments may be in the form of a dry powder (e.g. a lyophilized powder) which may be dissolved in the pharmaceutically acceptable diluent prior to administration. Suitably, for example the oligonucleotide may be dissolved in a concentration of 0.1-100 mg/mL, such as 1-10 mg/mL.

Compositions of the disclosure may be administered to a patient for the prevention or treatment of pain, such as chronic pain, neuropathic pain, inflammatory pain, spontaneous pain, or nociceptive pain. The oligonucleotides of the invention, or the conjugates, salts or pharmaceutical compositions of the invention may be for use as a local analgesic.

The pain which may be treated by the oligonucleotides of the invention, or the conjugates, salts or pharmaceutical compositions of the invention may be pain wherein the pain signal is in the peripheral nervous system. Indications associated with pain with a significant peripheral component include for example, diabetic neuropathies, cancer, cranial neuralgia, postherpetic neuralgia and post-surgical neuralgia.

Pain which may be prevented, treated or ameliorated using the oligonucleotide, conjugate, composition or salt of the invention may for example be selected from the group consisting of pain associated with inherited erythromelalgia (IEM), paroxysmal extreme pain disorder (PEPD), trigeminal neuralgia, neuropathic pain, chronic pain, but also general treatment of nociceptive (e.g. compression of a nerve), neuropathic pain (e.g. diabetic neuropathy), visceral pain, cancer pain, or mixed pain. The invention provides for the oligonucleotide, conjugate, composition or salt of the invention for the use for the prevention or for the treatment of pain, such as chronic pain, neuropathic pain, inflammatory pain, spontaneous pain, cancer pain, or nociceptive pain.

The disclosure provides methods for treating or preventing pain in a subject, such as a human, who is suffering from or is likely to suffer pain, comprising administering a therapeutically or prophylactically effective amount of an oligonucleotide, an oligonucleotide conjugate or a pharmaceutical composition of the invention to a subject who is suffering from or is susceptible to suffering from pain, such as cancer pain, osteoarthritis pain, chronic pain, neuropathic pain, inflammatory pain, spontaneous pain, or nociceptive pain, where the oligonucleotide is targeted to a sequence complementary to one of SEQ ID NOs: 1-141.

Dual-Knockdown Embodiments

Embodiments of the disclosure relate to therapeutic compositions for treating pain via multiple targets. The compositions include an oligonucleotide that hybridizes to RNAs from more than one genes for a sodium channel protein (e.g., human Nav1.7/Nav1.8) along a segment of the RNA that is at least about 75% complementary to one of SEQ ID NOs: 142-164 to thereby prevent translation of the RNA into the sodium channel protein. Note: SCN9A is NaV1.7; SCN10A is NaV1.8; and SCN11A is NaV1.9.

The oligonucleotide may have a sequence that is at least 80% similar to one of SEQ ID NOs: 142-164 (albeit in "gapmer" structure, with a DNA core and RNA wings). The outer wings of the oligonucleotide may include modified RNA chemistry, such as, for example, being made mostly or wholly of 2-methoxyethyl (2'-MOE) RNA bases. Preferred embodiments include a few (e.g., two to four) phosphodiester bonds within the wings with all other inter-base linkages being phosphorothioate. For example, the second, third, fourth, fifteenth, and seventeenth linkages (in the direction written in the sequences) may be phosphodiester, with all others being phosphorothioate. Notably in such embodiments, the outer-most linkages and all linkages involving a DNA base are preferably phosphorothioate, leaving three of the inter-RNA linkages to include either two or three phosphodiester linkages (balance being phosphorothioate). In a preferred embodiment, the composition includes copies of one more oligoncucleotides, each with a sequence given by one of SEQ ID NOs: 142-164, with a 5-9-5 (RNA-DNA-RNA) gapmer design, in which the outer-most inter-base linkages and all linkages involving a DNA base are phosphorothioate, and in which the other three inter-RNA linkages of each wing comprise either two or three phosphodiester linkages (balance being phosphorothioate).

The human Nav1.7/Nav1.8 dual knockdown sequences exemplified by SEQ ID NOs: 142-164 are each preferably provided as a 19-mer ASO gapmer design following a 5×9×5 configuration, with 9-base DNA core with 5' and 3' RNA-like wings. Preferably, the 5' and 3' wings at least substantially follow 2-methoxyethyl (2'-MOE) chemistry and the backbone linkages include a mixture of phosphorothioate (PS) and phosphodiester (PO) (e.g., outer-most inter-base linkages and all linkages involving a DNA base are PS, and in which the other three inter-RNA linkages of each wing comprise either two or three PS linkages, balance PO). In certain embodiments, the human Nav1.7/Nav1.8 dual knockdown comprises an oligonucleotide with a sequence as given by one of SEQ ID NOs: 142-164 and a gapmer composition as just described.

Of the dual knockdown sequences, a first preferred embodiment, dubbed group 1, is illustrated by SEQ ID Nos: 142-152, also described as Ref. No. (Target code/No.) 4/61-4/71. All the group 1 dual knockdown ASOs have 100% match with human SCN9A transcript and only have 1 nucleotide mismatch with human SCN10A. The indicated dual-knockdown ASO oligonucleotides of group 1 have a 5-9-5 gapmer design, with a 9-base DNA core and 5' and 3' RNA-like wings. The 5' and 3' wings include 2-methoxyethyl (2'-MOE) chemistry. The backbone includes a mixture of phosphorothioate (PS) and phosphodiester (PO), e.g., in which the second, third, fourth, fifteenth, and seventeenth linkages (in the direction written in the sequences) may be PO, with all others being PS. Preferably any of SEQ ID Nos: 142-152 have that backbone chemistry. Each of the sequences in this group 1 has zero mismatches to a target sequence in human SCN9A pre-RNA or mRNA and 1 mismatch to a target sequence in human SCN10A pre-RNA or mRNA.

Of the dual knockdown sequences, a second preferred embodiment is dubbed group 2, illustrated by SEQ ID NOs: 153-164, also described as Ref. No. (Target code/No.) 5/49-5/60. All the group 2 dual knockdown ASOs have 100% match with human SCN10A transcript and only have 1 nucleotide mismatch with human SCN9A. The indicated dual-knockdown ASO oligonucleotides of group 2 have a 5-9-5 gapmer design, with 9-base DNA core with 5' and 3' RNA-like wings. The 5' and 3' wings include 2-methoxyethyl (2'-MOE) chemistry. The backbone includes the mixture of phosphorothioate (PS) and phosphodiester (PO), e.g., in which the second, third, fourth, fifteenth, and seventeenth linkages (in the direction written in the sequences) may be PO, with all others being PS. Preferably any of SEQ ID NOs. 153-164 have that backbone chemistry. Each of the sequences in this group 2 has 1 mismatch to a target sequence in human SCN9A pre-RNA or mRNA and zero mismatches to a target sequence in human SCN10A pre-RNA or mRNA.

In certain dual-knockdown embodiments, the invention provides for an oligonucleotide of 10 to 30 nucleotides in length, which comprises a contiguous nucleotide sequence of 10 to 30 nucleotides in length with at least 90% complementarity, such as 100% complementarity, to a human NaV1.7 target nucleic acid and a human NaV1.8 target nucleic acid, and which is capable of inhibiting the expression of both NaV1.7 or NaV1.8 in a cell.

Figure 12:
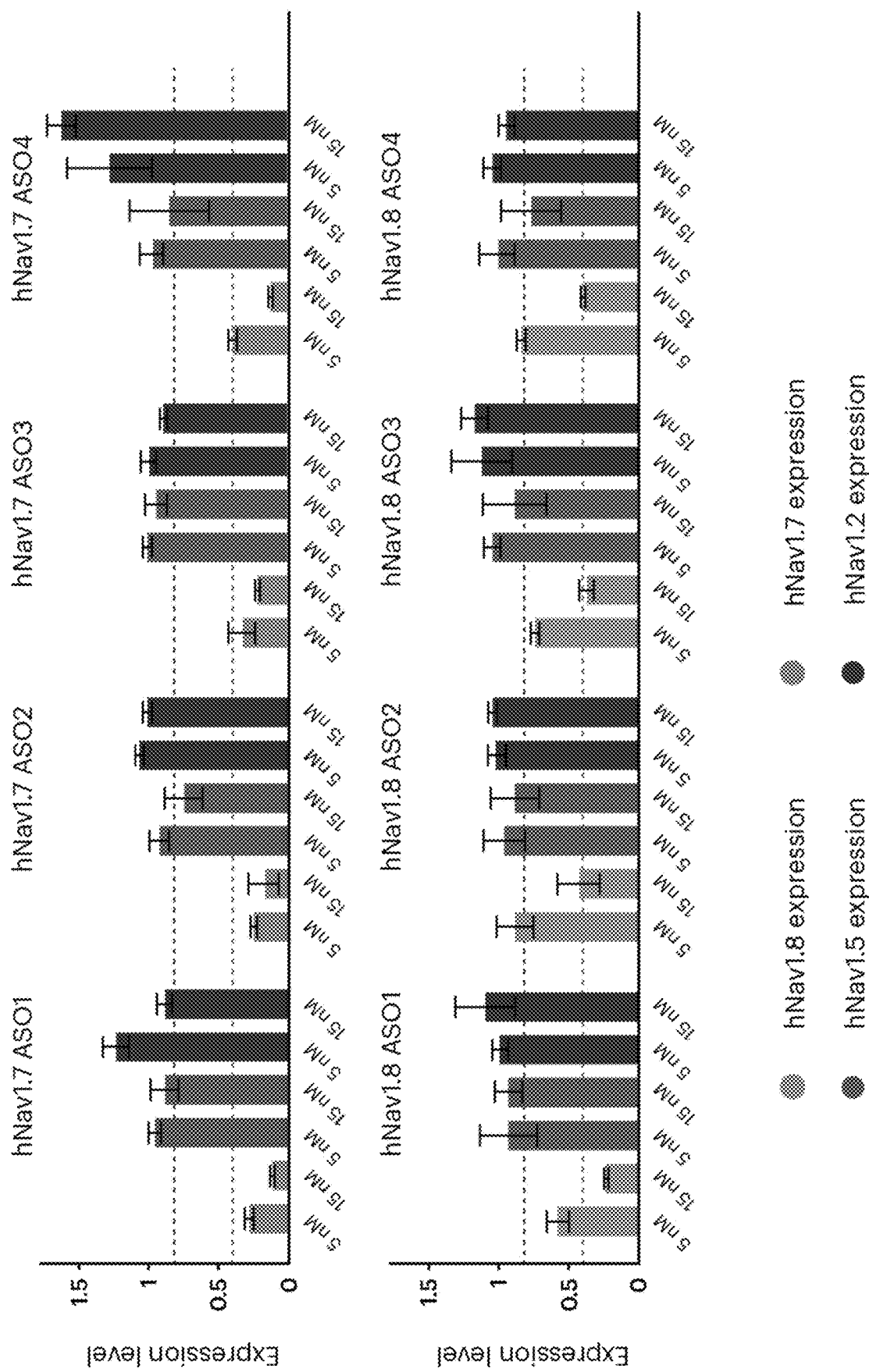
FIG. 12 shows that ASOs of the disclosure knockdown Nav targets.

FIG. 12 shows that ASOs of the disclosure provide potent and selective knockdown of multiple Nav targets. In the figure, the top graph shows comparative expression levels of NaV1.7 beside NaV1.5 and NaV1.2, when treated with four different ASOs (labelled ASO1, ASO2, ASO3, and ASO4) at 2 concentrations. The bottom graph shows comparative expression levels of NaV1.8 beside NaV1.5 and NaV1.2, when treated with those same four different ASOs (again, ASO1, ASO2, ASO3, and ASO4) at 2 concentrations.

The first group of six bars in the top panel shows that, at either 5 nM or 15 nM concentration of ASO1, expression of NaV1.7 was knocked down significantly compared to expression of NaV1.5 and NaV1.2. Unexpectedly, the first group of six bars in the bottom panel shows that, at either 5 nM or 15 nM concentration of ASO1, expression of NaV1.8 was knocked down significantly compared to expression of NaV1.5 and NaV1.2. That is, the left-most groups of six bars on the top and on the bottom panels show that ASO1 specifically knocks down expression of both NaV1.7 and NaV1.8, compared to NaV1.5 and NaV1.2. Looking at the top and bottom panels together, the second group of parts shows the same thing for ASO2; the third group of bars shows the same result for ASO3; and the fourth group of six bars shows the same result for ASO4. These data strongly show that ASOs of the disclosure are capable of inhibiting the expression of both NaV1.7 or NaV1.8.

Different Nav channels have different biophysical properties and roles in excitability.

Figure 13:
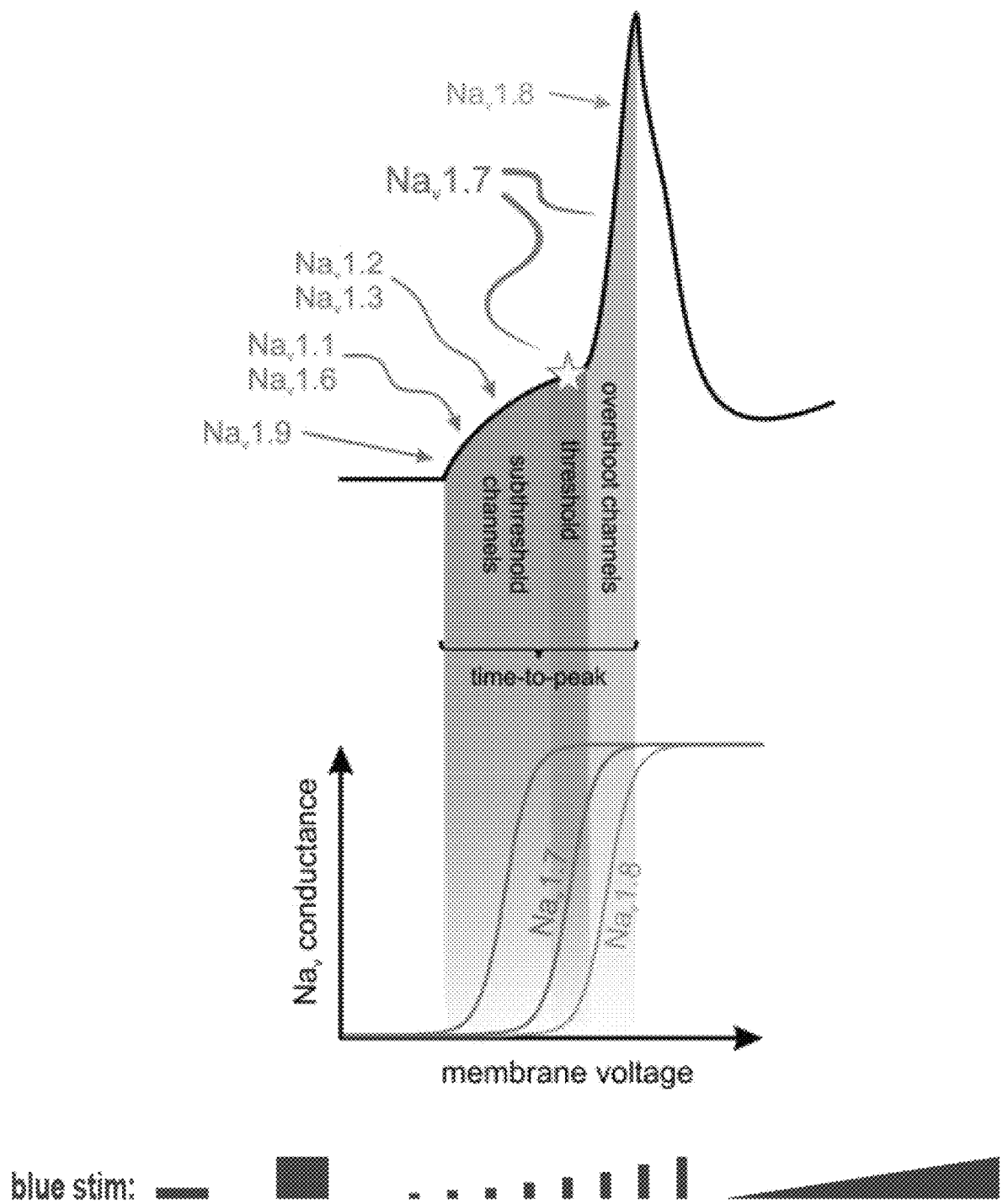
FIG. 13 shows Nav channels involved neural activity.

FIG. 13 shows which Nav channels are substantially or principally involved in excitability at threshold, sub-threshold, and above the threshold for neural activity. The data are obtained by using blue light and Optopatch constructs to stimulate neurons and measure sodium (Na) conductivity. Blue light stimulation protocols were used to characterize roles of each Nav in nociceptor firing. The data show that NaV1.7 and NaV1.8 are primary drivers of activity at and above threshold, and hence that those targets represent valuable targets for a therapeutic composition for treating pain. Here, the disclosure provides antisense oligonucleotide-based therapeutics against validated target Nav1.7 and Nav1.8.

What is claimed is:

1. A composition for treating pain, the composition comprising: an oligonucleotide that hybridizes to an RNA encoding a sodium channel protein along a segment of the RNA that is 100% complementary to a member selected from the group consisting of SEQ ID NOs: 1-164, wherein the oligonucleotide comprises a central DNA segment flanked by modified RNA wings.

2. The composition of claim 1, wherein the oligonucleotide hybridizes to, and knocks down expression of, one or more of NaV1.7, NaV1.8, and NaV1.9 pre-mRNA or mRNA.

3. The composition of claim 1, wherein a sequence of bases in the oligonucleotide has 100% identity to a member selected from the group consisting of SEQ ID NOs: 1-164.

4. The composition of claim 1, wherein a sequence of bases in the oligonucleotide is 100% identical to a member selected from the group consisting of SEQ ID NOs: 1-101, wherein the oligonucleotide can hybridize to, and induce RNase cleavage of, either NaV1.7 pre-mRNA or mRNA or NaV1.8 pre-mRNA or mRNA.

5. The composition of claim 1, wherein the composition comprises a plurality of therapeutic oligonucleotides each having a base sequence 100% identical to a member selected from the group consisting of SEQ ID NOs: 1-164, wherein each of the therapeutic oligonucleotides has a gapmer structure, wherein the plurality of therapeutic oligonucleotides are provided in a solution or carrier formulated for intrathecal injection.

6. The composition of claim 1, wherein the oligonucleotide comprises a central region of at least 10 DNA bases.

7. The composition of claim 1, wherein each modified RNA base of the modified RNA wings is selected from the group consisting of 2'-O-methoxyethyl RNA and 2'-O-methyl RNA.

8. The composition of claim 1, wherein the oligonucleotide comprises at least 15 bases.

9. The composition of claim 1, wherein the oligonucleotide comprises between 15 to 25 bases.

10. The composition of claim 1, wherein the oligonucleotide has a backbone comprising a plurality of phosphorothioate bonds.

11. The composition of claim 1, wherein the oligonucleotide has a base sequence that has been screened and determined to not meet a threshold match for any non-target transcripts in humans.

12. The composition of claim 1, wherein the oligonucleotide has a base sequence with 0 mismatches to a homologous segment in a non-human primate genome and no more than 5 mismatches in a homologous segment in a rodent genome.

13. The composition of claim 1, wherein when the composition is delivered to the dorsal root ganglion (DRG) neurons in vitro, the DRG neurons exhibit a dose-dependent knockdown of NaV1.7, NaV1.8, or NaV1.9.

14. The composition of claim 1, wherein the oligonucleotide has a base sequence with 100% match to a member selected from the group consisting of SEQ ID NO: 1-141, with bases linked only by phosphorothioate linkages, the oligonucleotide further comprising a central 10 DNA bases flanked by a 5' wing and a 3' wing, the 5' wing and the 3' wing each comprising five consecutive 2' modified RNA bases.

15. The composition of claim 1, wherein the oligonucleotide has a base sequence matching a member selected from the group consisting of SEQ ID NO: 1-141, with a majority of inter-base linkages comprising phosphorothioate linkages, the oligonucleotide further comprising a central 10 DNA bases flanked by a 5' wing and a 3' wing, the 5' wing and the 3' wing each comprising five consecutive 2' MOE RNA bases.

16. A composition comprising a plurality of copies of a plurality of distinct therapeutic gapmers of one of the preceding claims in a carrier formulated for intrathecal administration.

17. The composition of claim 1, wherein the oligonucleotide is a gapmer that exhibits at least 25% better Nav knockdown than a control gapmer in an assay using DRG neurons in vitro.

18. The composition of claim 1, wherein one or more bases in said RNA are methylated.

19. The composition of claim 18, wherein said methylated bases are selected from 5-methylcytosine and 5-methyluracil (thymine).

* * * * *